United States Patent
Millington

(10) Patent No.: US 8,097,465 B2
(45) Date of Patent: Jan. 17, 2012

(54) SENSOR WITH HOLOGRAPHIC MULTIPLEXED IMAGE DISPLAY

(75) Inventor: Roger Bradley Millington, Huntingdon (GB)

(73) Assignee: Smart Holograms Limited, Cambridge (GB)

( * ) Notice: Subject to any disclaimer, the term of this patent is extended or adjusted under 35 U.S.C. 154(b) by 126 days.

(21) Appl. No.: 12/133,214

(22) Filed: Jun. 4, 2008

(65) Prior Publication Data
US 2008/0241952 A1 Oct. 2, 2008

Related U.S. Application Data

(63) Continuation of application No. 10/169,502, filed as application No. PCT/GB01/00061 on Jan. 8, 2001, now abandoned.

(30) Foreign Application Priority Data

Jan. 7, 2000 (GB) ........................... 0000209

(51) Int. Cl.
*G01N 21/00* (2006.01)
(52) U.S. Cl. ............... 436/164; 436/518; 430/1; 430/2
(58) Field of Classification Search .................. None
See application file for complete search history.

(56) References Cited

U.S. PATENT DOCUMENTS

| | | | |
|---|---|---|---|
| 3,917,453 A | 11/1975 | Milligan et al. | |
| 4,059,407 A | 11/1977 | Hochstrasser | |
| 4,788,115 A * | 11/1988 | Long et al. | 430/2 |
| 5,242,828 A | 9/1993 | Bergström et al. | |
| 5,401,667 A | 3/1995 | Koike | |
| 5,436,161 A | 7/1995 | Bergström et al. | |
| 5,514,501 A | 5/1996 | Tarlov | |
| 5,571,401 A | 11/1996 | Lewis et al. | |
| 5,611,998 A | 3/1997 | Aussenegg et al. | |
| 5,989,923 A | 11/1999 | Lowe et al. | |
| 6,277,330 B1 | 8/2001 | Liu et al. | |
| 6,689,316 B1 | 2/2004 | Blyth et al. | |

FOREIGN PATENT DOCUMENTS

| | | |
|---|---|---|
| WO | WO 95/26499 | 10/1995 |
| WO | WO 98/10334 | 3/1998 |
| WO | WO 98/43086 | 10/1998 |

(Continued)

OTHER PUBLICATIONS

Marshall et al. "Analyte-responsive holograms for (bio)chemical analysis". 2006. J. Phys.:Condens. Matter. vol. 18, pp. S619-S626.*

(Continued)

*Primary Examiner* — Yelena G Gakh
*Assistant Examiner* — David Weisz
(74) *Attorney, Agent, or Firm* — Hamilton, Brook, Smith & Reynolds, P.C.

(57) ABSTRACT

A holographic sensor comprising a thin film polymer matrix that undergoes a change in response to a substance to be sensed, the matrix containing within its volume a set of two or more holographic recordings, each recording providing a holographic image when the sensor is illuminated, wherein the presence or appearance of each image is visible to the eye as a function of the response of the sensor to the substance to be sensed. The images provide the dynamic range of the sensor. Such a sensor can be used to provide a visible image that changes or appears to the eye in response to an analyte.

30 Claims, 28 Drawing Sheets

FOREIGN PATENT DOCUMENTS

WO          WO 99/63408          12/1999

OTHER PUBLICATIONS

Mayes et al. "A holographic sensor based on a rationally designed synthetic polymer". 1998. J. Molecular Recognition. vol. 11. pp. 168-174.*

Office Action dated Dec. 14, 2004, U.S. Appl. No. 10/169,502.
Office Action dated May 31, 2005, U.S. Appl. No. 10/169,502.
Office Action dated Dec. 14, 2005, U.S. Appl. No. 10/169,502.
Office Action dated Jun. 19, 2006, U.S. Appl. No. 10/169,502.
Notice of Panel Decision from Pre-Appeal Brief Review dated Nov. 1, 2006, U.S. Appl. No. 10/169,502.
Examiner's Answer dated Aug. 3, 2007, U.S. Appl. No. 10/169,502.
Decision on Appeal dated Jun. 18, 2008, U.S. Appl. No. 10/169,502.

* cited by examiner

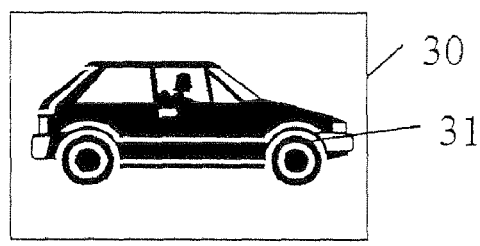
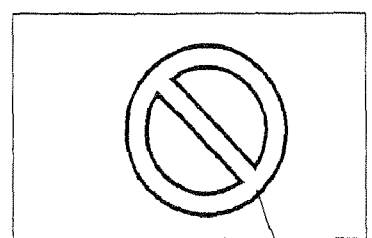
Fig. 3a          Fig. 3b
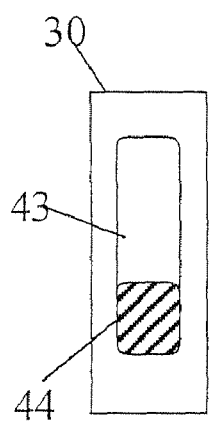
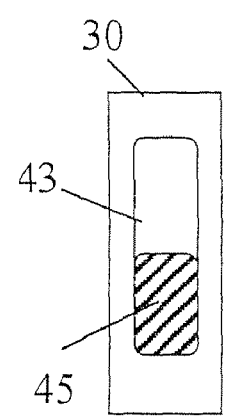
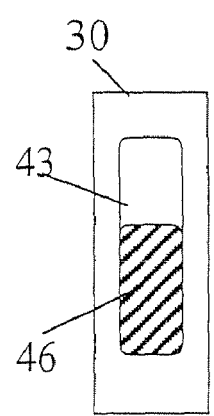
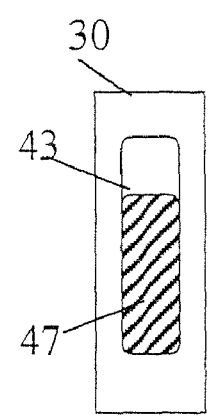
Fig. 4a     Fig. 4b     Fig. 4c     Fig. 4d
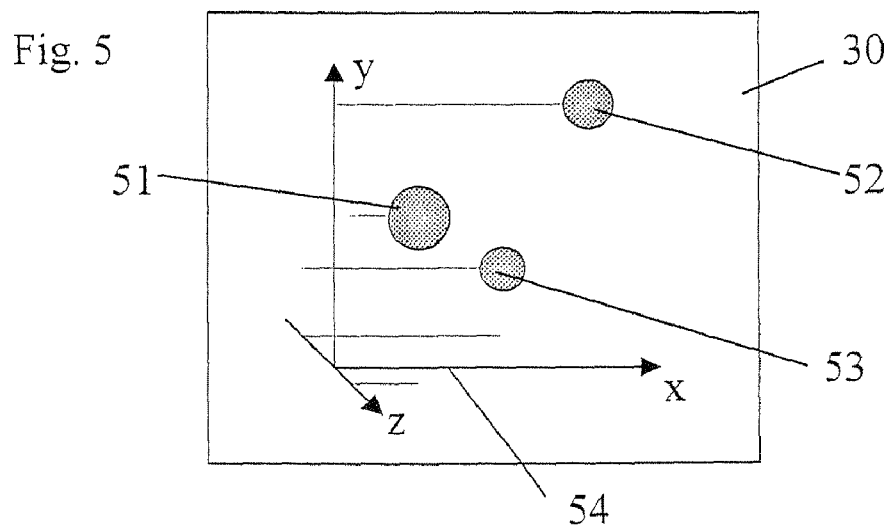
Fig. 5

BRAGG EQUATION  $\lambda pk = 2.D n. \cos(\theta f - \theta B)$

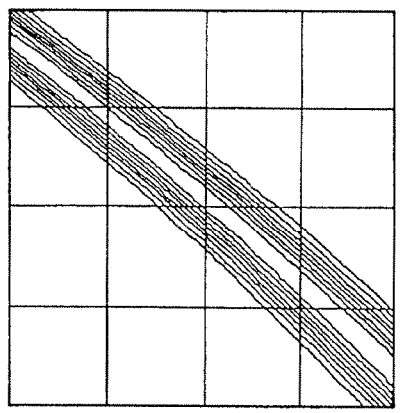
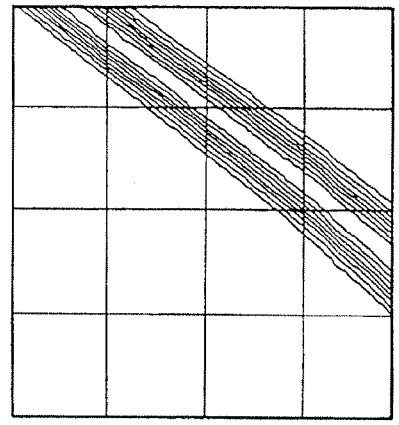
Fig. 16a
Fig. 16b
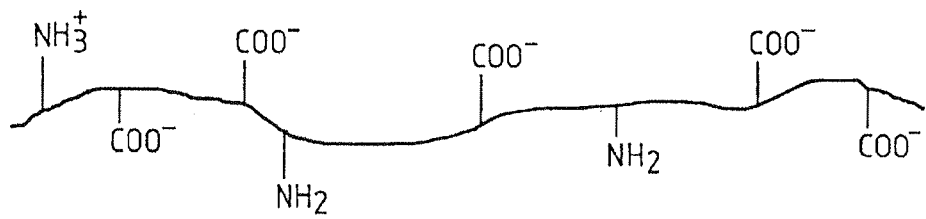
Fig. 17a
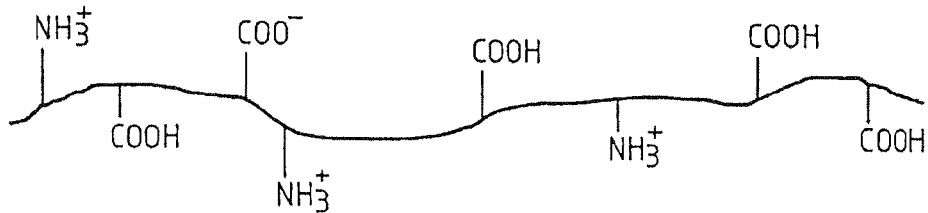
Fig. 17b

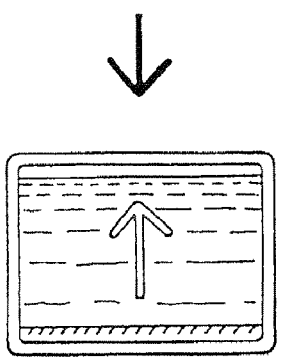
Fig. 27
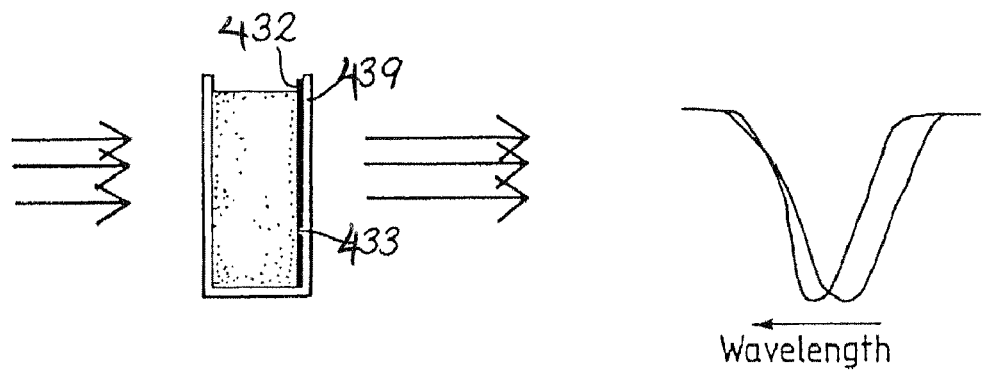
Fig. 28a
Fig. 28b
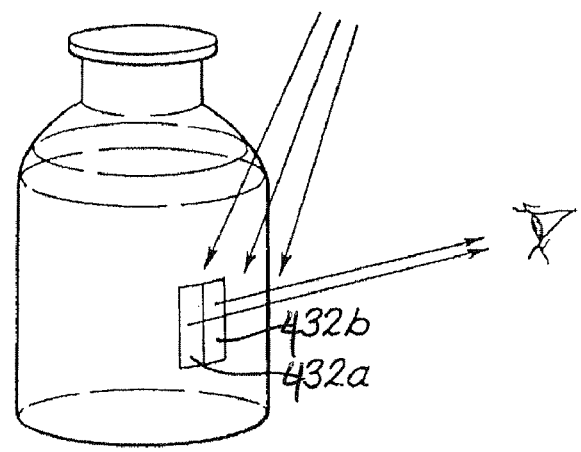
Fig. 29

SENSOR WITH HOLOGRAPHIC MULTIPLEXED IMAGE DISPLAY

RELATED APPLICATIONS

This application is a continuation of U.S. application Ser. No. 10/169,502, filed Jul. 23, 2002 now abandoned, which is the U.S. National Stage of International Application No. PCT/GB01/00061, filed on Jan. 8, 2001, published in English, which claim priority under 35 U.S.C. §119 or 365 to UK Application GB 0000209.7 filed Jan. 7, 2000. The entire teachings of the above applications are incorporated herein by reference.

FIELD OF THE INVENTION

The present invention relates generally to sensors and more particularly to a holographic multiplexed image sensor.

BACKGROUND OF THE INVENTION

Chemical sensors and biosensors in the form of volume holograms made in specially made polymer layers are known. WO-A-95/26499 discloses a sensor which comprises a reflection hologram made in a thin film of polymeric material where the polymer interacts with a substance to be detected so as to alter the optical properties of the hologram, thereby providing a means for detecting or quantifying that substance. More generally, this reference and also WO-A-99/64308 disclose the concept of a volume hologram sensor which provides a measurable or observable optical change.

Within the art of holography, multiple holographic images and methods for creating them in a single holographic recording material are known. U.S. Pat. No. 4,509,818 discloses a method of making a three-dimensional holographic multiplexed image from a series of two-dimensional images. U.S. Pat. No. 5,103,325 discloses a method of holographically recording a series of two-dimensional images such that the viewed holographic images are observed separately and distinctly from each other. U.S. Pat. No. 5,734,485 discloses a method of producing three-dimensional still or moving scene holograms including recordings of computer-generated scenes.

These known systems produce sets of holographic images which are multiplexed in a degree-of-freedom which is only spatial, where the images are intended to be viewable by an observer as an artificially-produced three-dimensional image or as a set of images separated in space over a corresponding set of angles of view. The optical properties of the material in which these holograms are made are intended to be invariant in time and they are not intended to be altered chemically when functioning normally.

SUMMARY OF THE INVENTION

An object behind the present invention is to provide a volume hologram sensor which provides a multiplicity of holographic images, where the set of images is multiplexed in the degree-of-freedom which is the dynamic detection range of the sensor, where each image, when visible, represents a finite region of the dynamic detection range.

According to a first aspect of the present invention, a holographic sensor comprises one or more films each containing within its volume a set of two or more holographic recordings, each recording providing a reflected holographic image when the sensor is illuminated by light and where each image is visible to the eye as an indicator that the sensor is showing a response to a predetermined range of concentration of a substance or group of substances to be sensed. More particularly, the presence or appearance of each image is visible to the eye as a function of the response of the sensor to a substance to be sensed; that response may involve the appearance or disappearance, or a change in, a visible image.

Typically, each image in the set of images has a reflection spectrum characterised by its location in the invisible or visible spectrum of light. The location in the spectrum may be unique to each image, such that the images are separable by wavelength-selective means and are therefore wavelength-multiplexed.

BRIEF DESCRIPTION OF THE DRAWINGS

FIGS. 3a and 3b are each schematic drawings of a holographic sensor showing changing pictorial images.

FIGS. 4a to 4d are each schematic drawings of a holographic sensor illustrating a changing image in correspondence with the amount of substance detected.

FIG. 5 is a schematic drawing of multiple features of a three-dimensional image.

FIGS. 16a and 16b show contour plots of passband characteristic of reflected intensity, as a function of wavelength and incident angle.

FIG. 16a shows plots where there is no size change.

FIG. 16b shows a plot where the size change (wX) is 10%.

FIGS. 17a and 17b show diagrammatic sketches of gelatin strands with amino and carboxyl groups.

FIG. 18a shows cross-links between gel strands to harden gel.

FIG. 18b shows cross-links between gel strands as a sensing mechanism.

FIG. 18c shows diagrammatically the interaction of charged groups contributing to the strength of the gel.

FIG. 18d shows diagrammatically the effect of charge shielding by an attached molecule.

FIG. 27 shows diagrammatically hologram construction in a cuvette with 0° reflection.

FIG. 28a shows diagrammatically hologram replay in the cuvette of FIG. 27.

FIG. 28b is a graph of signal absorbance when replaying the hologram of FIG. 27.

FIG. 29 shows diagrammatically test strips attached to the inside of a bottle containing a liquid reagent.

DETAILED DESCRIPTION OF THE INVENTION

Figure 1:
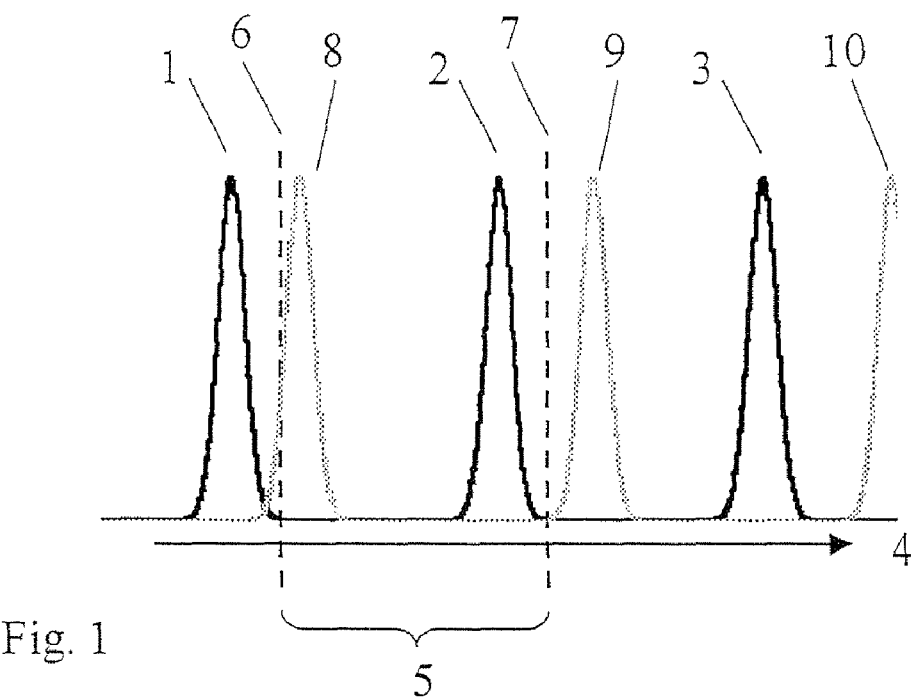
FIG. 1 shows an example of the multiple spectral peaks of a multiplexed reflection hologram, typical of those exhibited by a multiplexed holographic sensor.

A sensor of the invention may be constructed and used in the manner generally described in WO-A-95/26499 or WO-A-99/63408. The contents of these publications, and other documents referred to herein, are incorporated by reference. Thus, for example, the matrix in which the holographic images are formed may be a chemically sensitive polymeric film, or it may comprise a plurality of films that are generally parallel (adjacent or separated by another type of layer). In such an arrangement, each film may provide its own dynamic range, and each film may be designed to detect or measure a specific substance. Each film may present one image or a sub-set of images with its own place in the dynamic range of the sensor; the dynamic range is created by having a plurality of films which provide a plurality or set of images.

More particularly, a sensor of the invention can be in the form of a polymer film or multiple films coated or otherwise disposed onto a transparent or opaque, flexible, semi-rigid or rigid substrate such as glass, plastic, paper or metal. The substrate can be printed, engraved or otherwise marked with a pattern or alpha-numerical markings so as to provide a reference to the holographic images.

The sensor can, alternatively, be provided in or onto a material which is a component of or constitutes a device such as contact lens, spectacle lens, optical window into a reaction vessel, instrument display window, domestic window, visual display device or any component where an ambient substance is to be monitored or detected.

The sensor can, alternatively, be provided in or onto a material which is a component of or constitutes an item of clothing so as to confer the ability to monitor or detect ambient substances or physiological substances related to the wearer of the clothing.

The invention can be in the form of multiple layers of holographic polymer films which are interleaved with other types of layers acting as transport media for substances to be detected or monitored or other components of a sample.

Illumination of the hologram(s) by ambient artificial or natural light can be directly onto the plane surfaces or, alternatively, can be provided by illuminating the polymer films along their edges, where the holograms are commonly known as "edge-lit" holograms.

A polymer film which is a sensitive element of the invention may be directly sensitive to an ambient substance or it may be sensitive to the product of a reaction or interaction between the ambient substance and one or more other ambient substances or substances which are provided specifically as components of the holographic sensor assembly. Such a film may be described herein as chemically sensitive, but this is for the purpose of illustration only.

Any of a variety of substances or analytes may be detected by means of the invention, including but not limited to those discussed in the prior art; reference herein to "a substance" includes the use of two or more such substances. Examples of analytes are water, organic liquids, ions, haptens, nucleotides, cells, aldehydes, enzymes, proteins, gases, metabolites, viruses, bacteria, fungi and yeasts. The analyte or a carrier medium may interact with the holographic matrix. In particular examples, the analyte is in liquid, e.g. an enzyme or ethanol in water, or water in an organic solvent.

In a preferred embodiment of the invention, each image from the set of the pictorial images that can be viewed depicts subject matter which is relevant to the sensor application. Each image may depict subject matter which is relevant to the response status indicated by the sensor.

The image may change from one picture to another in relation to the concentration of one or more substances to be detected by the sensor. The change in the pictorial image may be restricted to one or more parts of the image. A change in the pictorial image which is restricted to part of the image may be due to a response to a specific substance to be detected, such that a change in another part of the image is due to a response to another specific substance to be detected. Each part of the image which may be changed may be located anywhere in the three dimensions of the holographic image.

In another preferred embodiment of the invention, the set of images shows a sequence of numerical information which appears in a sequence corresponding to the concentration of one or more substances detected by the sensor. Preferably, the response of the sensor is calibrated so that the numerical images show numerical quantities which correspond directly with the concentration of a substance detected by the sensor.

In another preferred embodiment of the invention, the set of images shows a sequence of alphabetical information which appears in a sequence corresponding to the concentration of a substance detected by the sensor. Preferably, the alphabetical information is in the form of messages which are relevant to the sensor application. The response of the sensor may be calibrated so that the alphabetical information is in the form of messages which correspond directly with the concentration of a substance detected by the sensor.

In another preferred embodiment of the invention, each image of the set of images comprises an indicating feature which has a specific location, in the space of the image, corresponding to the concentration of a substance detected by the sensor. This is an example of a virtual instrument.

Preferably, the image or indicating feature is a shape. Alternatively, the indicating feature is a picture or is alpha-numerical.

The spatial degree of freedom of the location of the indicating feature may be parallel to the plane of the polymer film. Alternatively, the spatial degree of freedom of the location of the indicating feature is not parallel to the plane of the polymer film but is, instead, in the depth of the image which is an optional characteristic of a holographic image.

Preferably, the location of the indicating feature in either case is marked with reference to a visible scale. The visible scale may be provided as a holographic image provided by a hologram recorded in the same polymer layer as that which provides the indicating feature. Alternatively, the visible scale may be created by a holographic image provided by a different polymer layer from that which provides the indicating feature.

The visible scale may be incorporated with the polymer layer by photographic means. Alternatively, the visible scale may be printed onto the surface of the holographic element, or it may be printed onto a surface which is located adjacent to but separate from the holographic element.

Preferably, the visible scale which is provided as a holographic image is invariant with the concentration of the substance detected by the sensor.

A holographic sensor can provide any combination of pictorial, alphabetical, numerical or spatially-indicating means of displaying the holographic response. Further, an array of holographic sensors may be provided, each providing any combination of the above pictorial, alphabetical, numerical or spatially-indicating means of displaying the holographic response to a multiplicity of substances to be detected or multiplicity of groups of substances to be detected.

Preferably, each element of an array of holographic sensors has a unique response characteristic to the substances to be detected.

The visible display provided by an array of holographic sensors may present an overall pattern which corresponds to the relative concentrations of substances to be detected. The pattern displayed by an array of holographic sensors may be pictorial, numerical or alphabetical. An alphabetical pattern displayed by an array of holographic sensors may represent a message which is relevant to the relative concentrations of substances to be detected.

In any of the above cases, the discrimination of any one visible image from its neighbours in a set of images presented by the holographic sensor can be provided by creating a significant separation in the peak reflected wavelength provided by each image from that of its neighbours.

The discrimination of any one visible image from its neighbours in a sequence of images presented by the holographic sensor may be improved by providing a colour transmission filter located between the light source and a chemically-sensitive polymer film containing the holographic recordings, or between the eye used to view the holographic image and the film, or immediately adjacent to the film but between the film and the eye.

The colour transmission filter may be an integral feature of the material to which a chemically-sensitive polymer film is attached. Alternatively, the colour transmission filter may be an integral feature of the chemically-sensitive polymer film. In any of the above holographic sensors, a colour transmission filter increases the number of multiplexed images for any given dynamic range of response of the sensor, by permitting each image to be closer in peak wavelength to that of its immediate spectral neighbour.

According to a further aspect of the present invention, a method for creating a holographic sensor which has a multiplicity of wavelength-multiplexed images of one or more types chosen from pictorial, numerical, alphabetical, spatially-variant or array types, comprises exposing a polymer film, having already been photosensitised, to a sequence of holographic exposures over the course of a transition of the film from one state of swelling to another.

Each image of the set of images has a characteristic reflection spectrum which may have a peak wavelength which is different from that of other images in the set.

By way of example, the initial state of swelling may be set by placing the polymer film, before exposure, in a solution having a specific pH or ionic strength. Then the polymer film is immersed in a solution with a different specific pH or ionic strength, respectively, so that the film undergoes a transition of swelling or contraction, depending on its response.

Alternatively, the initial state of swelling is set by placing the polymer film, before exposure, in an immediate environment having a specific relative humidity. Then the relative humidity is altered so that the film undergoes a transition of swelling or contraction, depending on its response to relative humidity.

An alternative method for creating a holographic sensor which has a multiplicity of wavelength-multiplexed images of one or more types chosen from pictorial, numerical, alphabetical, spatially-variant or array types is to expose the photosensitive polymer film to each image so that the angle between the object and reference beams used to create the holographic recording is unique to that particular image.

A preferred method for exposing the photosensitive polymer film to a set of images is to expose it to a timed sequence of images of a transmission object where the transmission object is an optical device which is commonly known as a spatial light modulator and is controlled by an electronic signal source, e.g. a computer or a video camera. Preferably, the form of the object represented by the spatial light modulator is chosen from pictorial, numerical, alphabetical, spatially-variant or array types.

Preferably, the image provided by the spatial light modulator is controlled so as to have variable spatial features during the transition of swelling or contraction, so as to provide a means of providing a holographic sensor which has a spatially-variant response to a range of concentrations of a substance to be detected.

The present invention will now be described by way of example only with reference to the accompanying drawings. These drawings illustrate the changing display of two or more holographic images in response to a substance or group of substances to be detected by a holographic sensor.

In any form of the invention, there exist two or more reflected holographic images, each with a colour characterised by a narrow band spectrum having a peak wavelength. A peak wavelength arises from constructive interference between components of light reflected and diffracted from a periodic structure such as a holographic structure which is composed of a periodic distribution of complex refractive index contained within a thin film of holographic material which is commonly a polymer or similar matrix. In holography, such a periodic distribution of refractive index is commonly known as a distribution of fringes. The peak wavelength is defined mathematically by the Bragg equation which is $$\lambda_{pk}\{x,y,z\} = 2 \cdot n\{x,y,z\} \cdot \Lambda\{x,y,z\} \cdot \cos(\theta\{x,y,z\})$$

where n is an average index of refraction of the polymer film at a particular location defined generally by the co-ordinates x, y and z in the film, $\Lambda$ is the local spacing between adjacent fringes and $\theta$ is the angle of illumination of light which is incident on the fringes at that location in the film.

FIG. 1 shows a reflected intensity spectrum with a wavelength axis 4 showing three spectral peaks 1, 2 and 3 at one particular state in the dynamic range of the sensor. At this state, the only visible image is that characterised by the peak 2, situated in the region 5 of the spectrum which is normally visible to the eye, bordered by the ultra-violet end of the spectrum 6 and by the infra-red end of the spectrum 7. If the polymer film in which the sensor hologram is made swells during operation of the sensor then the characteristic peak wavelengths of the peaks 1, 2 and 3 all shift to longer wavelengths such that the image characterised by peak 1 originally invisible in the ultra-violet end of the spectrum becomes visible in a new spectral location 8. Similarly, the previously visible image characterised by the spectral peak 2 becomes invisible in the infra-red part of the spectrum, at a spectral location 9. Similarly, a response of the holographic sensor which is a contraction of the polymer film in which the sensor hologram is made is characterised by a shift of the peaks 1, 2 and 3 to shorter wavelengths.

Figure 2:
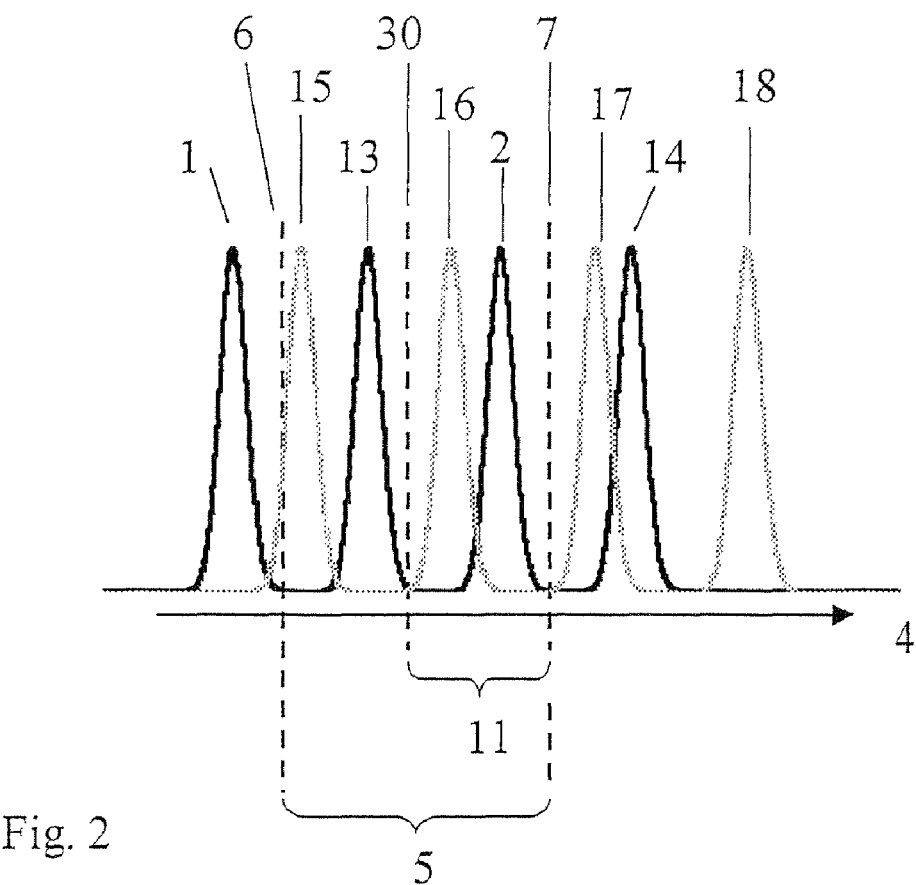
FIG. 2 shows another example of the multiple spectral peaks of a multiplexed reflection hologram typical of those exhibited by a multiplexed holographic sensor.

In an alternative form of the invention, more spectral peaks per region of the spectrum can be provided whilst maintaining discrimination between adjacent images. FIG. 2 shows a restriction of the region 5 of the spectrum which is available to be seen by eye or other detector to a narrower region 11 bounded by a lower end 30 set in this example by a long-wavelength pass filter and an upper end 7 at the upper end of the normally visible part of the spectrum 5. In general, a means of restricting the visible spectrum is not confined to a long wavelength pass edge filter but can be chosen from long wavelength pass filter, short wavelength pass filter, band-pass filter or any other optical device which restricts the detectable part of the whole spectrum. FIG. 2 shows a reflected intensity spectrum with a wavelength axis 4 showing four spectral peaks 1, 2, 13 and 14 at one particular state in the dynamic range of the sensor. At this state, the only visible image is that characterised by the peak 2, situated in the narrower region 11 of the spectrum which is visible to the eye. If the polymer film in which the sensor hologram is made swells during operation of the sensor then the characteristic peak wavelengths of the peaks 1, 2, 13 and 14 all shift to longer wavelengths such that the image characterised by peak 13 originally invisible in the ultra-violet end of the spectrum becomes visible in a new spectral location 16. As the new image characterised by the spectral peak 16 appears the original visible image characterised by the spectral peak 2 becomes invisible as it moves to a new spectral location 17. As further swelling occurs the image characterised by the peak 1 becomes visible in the spectral location 16, or some such similar location in the confined visible region 11. One purpose of providing more spectral peaks per region of the spectrum is to allow a visible change in image to occur in response to a small swelling or contraction of the polymer film in which the holographic images are recorded. Another purpose of providing more spectral peaks per region of the spectrum is to provide a greater number of images throughout the dynamic range of the holographic sensor.

A preferred form of the invention is illustrated in FIG. 3a which shows a schematic representing a holographic image 31 of a car provided by a holographic recording in a piece of holographic material 30. In this particular example, the car represents a purpose for which a holographic sensor may be designed, that of detecting the excessive presence of alcohol in the breath of an individual person. One way in which the device represented in FIG. 3a may be used is to have a previously invisible image which becomes visible when saturated with moisture from the breath. In another way of using the device, the image such as that illustrated 31, could be always visible if provided in a state of saturation. The detection of excess alcohol in the breath is indicated by the change of the image 31 in FIG. 3a to another image 32 in FIG. 3b where the image illustrates pictorially that the tested person should not drive. The illustrations are given by way of example only and do not preclude the use of other pictorial images to convey other messages and instructions for the purpose of the use described or for any other application which uses pictorial information to illustrate the relative response of the sensor before and after use.

Another preferred form of the invention is illustrated schematically in FIG. 4a which shows a holographic material 30 providing, under illumination, an image of a shape 43 with a part 44 which is differentiated from the scale 43 by having a different appearance by way of colour, shape or pattern. The response of the sensor is indicated by the change in the image segment 44 to that 45 shown in FIG. 4*b*, illustrating an increase in the presence of a substance which is detected by the sensor by occupying a greater part of the image 43. Sequential response to greater amounts of a substance detected is indicated by progressive changes in parts 44 to 47 of the image 43, illustrated in FIGS. 4*a* to 4*d*. In this example, the spatial changes of the image or parts of the image are key features of this preferred form of the invention. An example of a particular application which utilises these essential features of the invention is as a medical diagnostic device which shows an image of a stylised form of the human body where a part of the image appears to be illuminated to indicate a biochemical, metabolic or pathological condition relating to the relevant part of the body.

FIG. 4 illustrates a set of images where features of the images are located in a plane in space. The essential features of the invention are not limited to planar images but can, alternatively, be employed in three-dimensional holographic images. In another preferred form of the invention, the spatial changes of the holographic image or parts of the image are located in the three-dimensional space of the image. FIG. 5 shows a sensor made in a holographic material 30 which provides an image in three dimensions indicated by the axes 54 in x, y and z and having features 51, 52 and 53. The features 51, 52 and 53 can be made to appear or disappear or change in appearance by way of colour, shape or pattern as the visible means of observing the operation of the sensor.

Figures 6A, 6B, 6C, 6D, 6E:
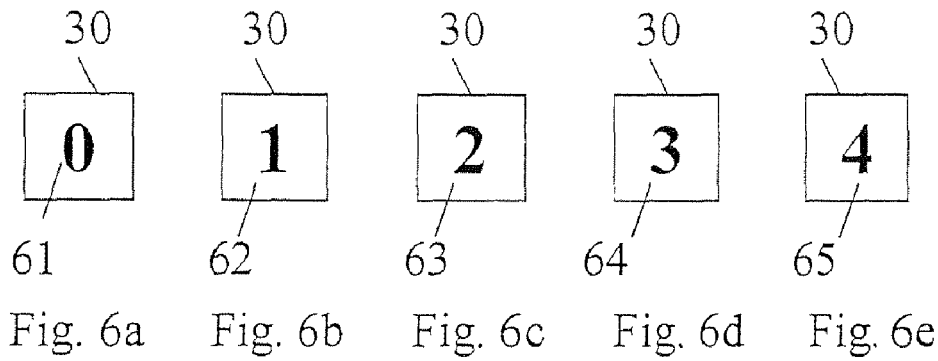
FIGS. 6a to 6e are each schematic representations of a holographic sensor with changing numerical images.
Figures 7A, 7B, 7C, 7D, 7E:
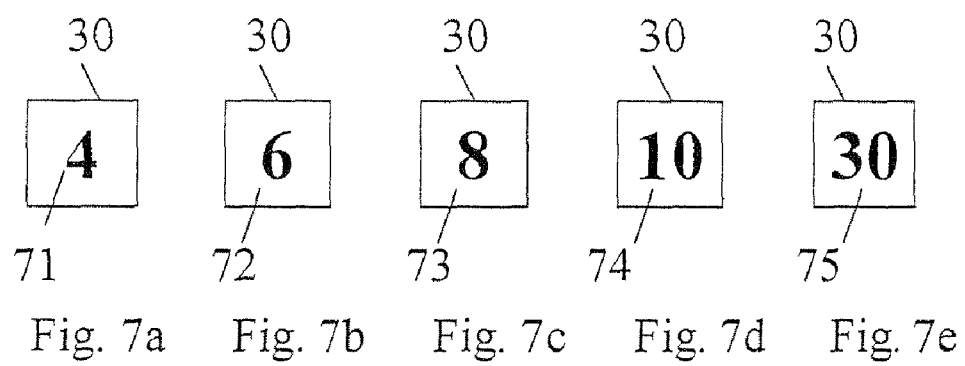
FIGS. 7a to 7e are each schematic representations of a holographic sensor with calibrated numerical images.

In any holographic sensor where an image or part of an image is made to change or become visible or invisible, the image or part of an image can have numerical form, as illustrated schematically in FIG. 6*a*. Numerical images 60-65 shown in FIGS. 6*a* to 6*e* illustrate a response in relation to the concentration of a substance or group of substances to be detected by the sensor. Alternatively, the numerical response of a holographic sensor can be calibrated to the concentration of a substance or group of substances to be detected, as illustrated in FIGS. 7*a* to 7*e*, by images 71-75.

Figures 8A, 8B, 8C, 8D, 8E:
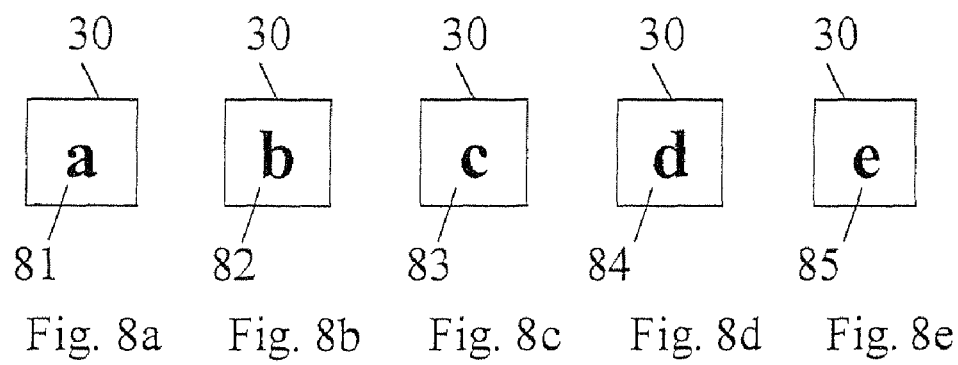
FIGS. 8a to 8e are each schematic representations of a holographic sensor with changing alphabetical images.

In any holographic sensor where an image or part of an image is made to change or become visible or invisible, the image or part of an image can have alphabetical form, as illustrated schematically in FIG. 8*a*. Alphabetical images 81-85 shown in FIGS. 8*a* to 8*e* illustrate a response in relation to the concentration of a substance or group of substances to be detected by the sensor.

In any holographic sensor, the images can optionally show a combination of numerical or alphabetical information relating to the application for which the sensor is intended.

Figure 9A:
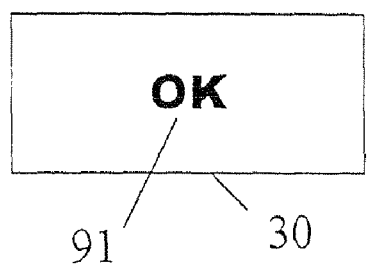
FIGS. 9a and 9b are each schematic representations of a holographic sensor illustrating changing images in the form of messages relating to the application of the sensor.
Figure 9B:
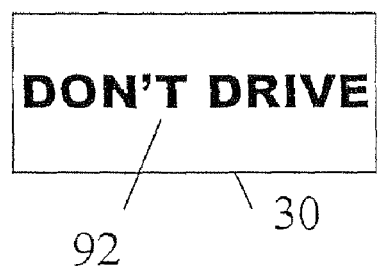

In any holographic sensor which presents alphabetical information, the message which is provided can be related to the application for which the sensor is intended. An example of a holographic sensor for breath alcohol is illustrated in the schematic of FIG. 9*a* which shows a message 91 indicating that the measured level is within bounds accepted by predetermined rules. The schematic of FIG. 9*b* illustrates an example of a message 92 which indicates that the measured level falls outside bounds accepted by predetermined rules.

Figure 10A:
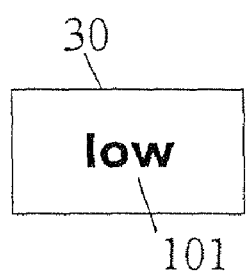
FIGS. 10a to 10c are each schematic representations of a holographic sensor illustrating changing images in the form of messages relating to the amount of substance or substances being detected.
Figure 10B:
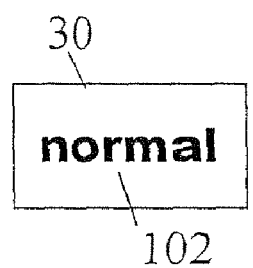
Figure 10C:
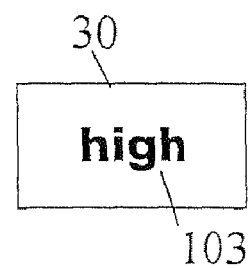

In any holographic sensor which provides alphabetical information, the message which is provided can be related to the concentration of substance or group of substances to be measured. FIG. 10*a* shows an alphabetical image 101 which indicates a low detected level of substance or group of substances. FIGS. 10*b* and 10*c* indicate, respectively, normal and high levels, by images 102 and 103. Alternatively, the messages provided can be an indicator as to the course of action to be followed as a consequence of carrying out the test provided by the holographic sensor.

The presentation of simple messages in the fashion provided by holographic sensor devices provides an unambiguous and easily understood result and is particularly suitable for rapid tests or use by unskilled people in a variety of healthcare, consumer or clinical applications though other applications areas are included.

Figure 11:
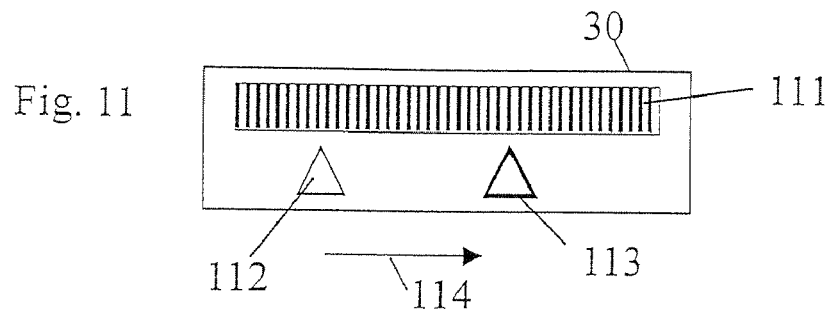
FIG. 11 is a schematic representation of a holographic sensor illustrating a changing image in the form of a moving indicator against a fixed scale.

In another preferred form of the invention, illustrated schematically in FIG. 11, each of the multiplexed holographic images is in the form of a pointing indicator. A series of such indicators is multiplexed according to methods described above such that, preferably, only one is visible at any one response state of the sensor. In the example shown in FIG. 11, just two of the indicator images 112 and 113 are shown, though a series of images separated spatially along the direction 114 provides a sequence related to the concentration of a substance or group of substances to be quantified. The pointing indicators 112 and 114 and others not shown in the diagram refer to a scale 111 which can be pictorial or numerical. A numerical scale 111 provides a means of quantifying the response of the sensor. The scale 111 can be chosen from the following types: printed adjacent to the holographic material, printed onto the holographic material, printed on a separate material under the holographic material, photographically created separate to the holographic material, photographically created within the holographic material, holographically created within the holographic material, holographically created in a separate holographic material from that which serves as the sensor material, though the list is not exclusive.

Figure 12:
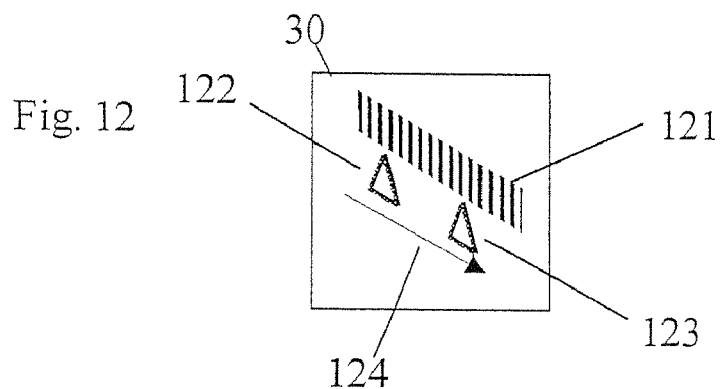
FIG. 12 is a schematic representation of a holographic sensor illustrating a changing image in the form of an indicator moving in the depth of the image against an image of a scale located in the depth of the image.

In another preferred form of the invention, illustrated schematically in FIG. 12, each of the multiplexed images is in the form of a pointing indicator which appear to be arranged in three dimensions, out of the plane of the holographic material 30. The characteristic depth which is optionally provided by holographic images is utilised in this form of holographic sensor. A series of such indicators is multiplexed according to methods described above such that, preferably, only one is visible at any one response state of the sensor. In the example shown in FIG. 12, just two of the indicator images 122 and 123 are shown, though a series of images separated spatially along the direction 124 in three spatial dimensions provides a sequence related to the concentration of a substance or group of substances to be quantified. The pointing indicators 122 and 124 and others (not shown) refer to a scale 121 which can be pictorial or numerical. A numerical scale 121 provides a means of quantifying the response of the sensor. The scale 121 is preferably itself a holographic image which is aligned with the sequence of multiplexed pointing indicator images though it can be chosen from the following types: printed onto the holographic material, printed on a separate material under the holographic material, photographically created separate to the holographic material, photographically created within the holographic material, holographically created within the holographic material, holographically created in a separate holographic material from that which serves as the sensor material, though the list is not exclusive. Some benefits of using three-dimensional holographic images in a holographic sensor are that the area of the holographic material can be reduced, allowing test sample volumes to be reduced, manufacturing cost to be reduced and space to be saved.

Figure 13:
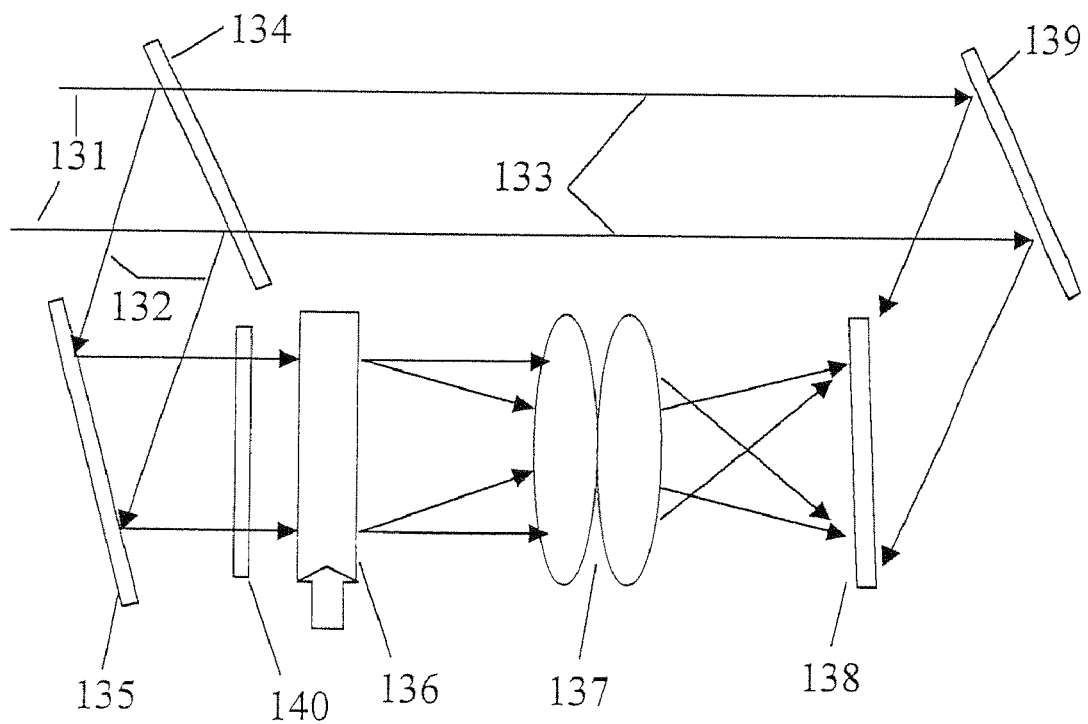
FIG. 13 is a schematic of an optical layout which can be used to expose a photosensitive holographic film or plate to multiple images with the purpose of making a wavelength multiplexed holographic sensor.

A preferred method for constructing the multiplexed images for the purpose of providing a holographic sensor is to use a two-beam image-hologram process such as that illustrated by way of example in the schematic of FIG. 13. A laser beam 131 is split into two beams 132 and 133 by a beam-splitter 134. One of the beams 132 is directed by a mirror 135 onto a transparent object 136 via an optional light diffuser 140. Preferably, the transparent object 136 is a spatial light modulator which is a video display device which provides an image under computer control. Alternatively, the transparent object 136 can be a photographic transparency. A benefit of using a computer-controlled spatial light modulator is that the transparent objects it provides as images to be recorded holographically can be rapidly changed in order to create the sequence of holographic images. The illuminated transparent object 136 is located at the object plane of an imaging system 137 which is a set of one or more lenses which provides an image of the object 136 at an image plane where a holographic recording material 138 is situated. The second laser beam 133 is directed, in this example, by a mirror 139 onto the holographic recording material 138 and thus acts as a reference beam (in holographic terminology). The image and the reference beams combine to produce an interference pattern in the holographic recording material 138 in such a way as to allow it to be retained by the material. Two examples of methods of recording a holographic interference pattern are by further chemical processing, if a silver-based recording material, or by using a photo-polymer material and appropriate laser wavelength. An essential feature of this aspect of the invention is that the state of swelling of the holographic recording material 138 is controllable by some means chosen from pH, ion concentration, humidity, water activity or any other means of altering the thickness of the holographic recording material. At each state of swelling of the material a different holographic image is created by the means described until a complete set has been recorded as a set of multiplexed images which display the response of a holographic sensor in the formats described above.

The sensor of the present invention may be constructed and used in the manner generally described in WO-A-95/26499, which provides a sensor comprising: a holographic element, which comprises a support medium supporting a hologram, wherein at least one optical characteristic of said holographic element varies as a result of a variation of a physical property occurring throughout the bulk of the holographic support medium characterised in that said variation in a physical property arises as a result of a biochemical reaction between the support medium and a species to be detected.

The biochemical reaction may involve a chemical reaction with a known compound or element. A suitable species is advantageously disposed on the surface of, or throughout the volume of, the sensor.

The physical property of the holographic element which varies may be its volume, shape, density, viscosity, strength, hardness, charge hydrophobicity, solvent swellability, integrity or any other physical property. Variation(s) of the, or each, physical property, in turn, cause(s) a variation of an optical characteristic, such as polarisability, reflectance, refractance or absorbance of the holographic element.

The hologram may be disposed on or in, part of or throughout the bulk of the volume of the support medium. An illuminating source of non-ionising radiation, for example visible light, may be used to observe variation(s) in the, or each, optical characteristic of the holographic element.

The physical property of the support medium which varies is preferably its volume. Alternatively the property which varies is the ability of the support medium to support a regularly-spaced distribution of complex index of refraction. The first of the aforementioned properties may be varied upon absorption of, or removal of, a liquid, such as water. The second property may be varied by chemical or biochemical action on the support medium.

Preferably the sensor includes a holographic element comprising a medium containing a spatial distribution of modulated complex index of refraction, which can be modified by the addition of an analyte species, such that the spectral and/or directional nature of incident radiation is modified in dependence upon a variation in said spatial distribution of modulated complex index of refraction.

Preferably the sensor comprises at least one species adapted to vary the distribution of modulated complex index of refraction upon interaction of the analyte species with a compound or element. The term modulated complex index of refraction is described below. Interaction may be chemical or physical. If the interaction is chemical it may be advantageous to have a specific binding conjugate of the analyte species disposed throughout at least part of, or all of, the support medium, or another component of the sensor.

Non-ionising radiation may be affected in one or more different ways. Preferably non-ionising radiation experiences a phase shift as a result of modification to the distribution of complex index of refraction arising from a change in spacing between peaks of a distribution supported in part, or throughout the volume of, the support medium.

More than one hologram may be supported on, or in, a sensor. Means may be provided to detect the, or each, variation in radiation emanating from, and having interacted with, the or each hologram, arising as a result of a variation in the, or each, optical characteristic. The holographic elements may be dimensioned and arranged so as to sense two independent events/species and affect simultaneously, or otherwise, radiation in two different ways.

Different types of hologram exist. One or more of these may be produced in, or on, the holographic support medium. Some different types of hologram are described below.

The term modulated complex index of refraction in general in a holographic element can refer to the modulation of the complex argument in the mathematical expression describing the electric field for non-ionising radiation. Light may be considered in terms of one or more electric fields. It is convenient, for holographic purposes, to envisage the electric field of light in a medium as comprising two components: one real (R); the other imaginary (I). This system of nomenclature is standard in holography and is used within the present specification to describe the effect a holographic element has on incident, non-ionising radiation. For example, when a hologram causes interference, by division of wave fronts in a form of diffraction grating.

A holographic element with the properties of an AMPLITUDE hologram comprises a 3-D distribution (modulation) of a radiation-absorbing material wherein the distribution is a physical record of an original interference pattern. Peaks of the modulation are referred to as fringes. Absorption of a propagating E-field in space can be introduced mathematically into the argument of the wave function by the imaginary component (I) of the refractive index. This describes how field amplitude is reduced along the direction of propagation.

A holographic element with the properties of a PHASE hologram may comprise a 3-D distribution (modulation) of refractive index where the distribution is a physical record of the original interference pattern. The peaks of the modulation are referred to as fringes. The phase of a propagating E-field in space can be represented mathematically in the argument of the wave function by the real (R) component of refractive index.

A hologram can have the properties of a PHASE or an AMPLITUDE hologram or both simultaneously. Holograms can be further categorised into four distinct types which can co-exist in the same support medium. These are transmission, reflection, edge-lit and surface.

A TRANSMISSION hologram is one where the emergent rays leave the holographic support medium via the surface opposite to that by which incident rays enter. Fringes are usually inclined to the surface at a considerable angle, e.g. typically around 90 degrees.

A REFLECTION hologram is one where rays leave by the same surface at which incident rays enter. Fringes are usually substantially parallel to the surface of the holographic support medium (e.g. around 0 degrees).

EDGE-LIT holograms are ones where rays leave the hologram substrate or bulk of holographic support medium (e.g. glass plate) via a surface which is substantially 90 degrees to that via which incident rays enter. Fringes are usually angled with respect to the surface, typically around 45 degrees.

Of the aforementioned holograms, usually reflection or edge-lit holograms are of a so called THICK volume type if there are many fringes (i.e. modulation cycles) counted within the volume of the holographic support medium in a direction perpendicular to the surface of the holographic support medium. The fringe planes, which may be flat or curved, are termed Bragg planes. The theory of Bragg reflection is predominant.

THIN type holograms also exist, when there are relatively few fringes. A hologram can be in an intermediate volume regime between THIN and THICK. The extent of the regime increases with modulation depth.

A SURFACE hologram is one where the surface of a medium is contoured with an appropriate spatial amplitude and with a regularly spaced pattern so that it is capable of diffracting and/or reflecting light. This has the properties of another type of PHASE hologram by virtue of creating a path difference between diffracted and/or reflected rays arriving at a common point from each point on its surface. If such a surface is defined on a transparent medium then light transmitted through the medium is subjected to periodic phase changes across the surface due to the variation in optical path length imposed by the refractive index of the bulk of the medium.

The relationship between some important parameters and measurands in TABLE 1 below, have been investigated with regard to holographic structures. For example, Kogelnik (H. Kogelnik, "Coupled Wave Theory for Thick Hologram Gratings", Bell System Technical Journal, 48, 9, 2909-2947, November 1969) used coupled wave theory to describe Bragg diffraction in THICK optical holograms. Thus by judicious choice of dimensions, type(s) of hologram and which internal parameter(s) is/are to be varied, different measurands may be observed. TABLE I is given to assist the skilled person to select which parameter may be varied. It is not intended to provide an exhaustive list of parameters, nor are the following equations the only equations inter-relating the parameters.

TABLE 1

| Internal Parameters | Symbol | Measurands | Symbol |
|---|---|---|---|
| Refractive index | n | Peak wavelength diffracted | $\lambda_{pk}$ |
| Refractive index modulation | $n_o$ | Bandwidth | $\Delta\lambda$ |
| Fringe spacing | D | Diffraction efficiency | $\eta$ |
| Fringe angle | $\theta_f$ | Incident angle | $\theta$ |
| Grain size | $\phi g$ | Modulation transfer function | MTF |
| Absorption modulation | $\alpha_o$ | Bragg angle of incidence | $\theta_B$ |
| Medium thickness | t | | |

Equations 1 to 4 below relate some of the various parameters and measurands in TABLE 1. Visual or instrumental means may be provided to sample one or more of these automatically or manually. One or more look-up table(s) and/or processing means may be incorporated electronically into a system arranged to detect a particular species Thus for example, the Bragg condition for optimum diffraction efficiency links incident angle ($\theta$), fringe angle ($\theta i$), optical spacing of the fringes (D) and peak response wavelength ($\lambda$pk) and is expressed in Eqn. 1 as:

$$\cos(\theta_B - \theta_f) = \lambda_{pk}/2 \cdot n \cdot D \qquad \text{Eqn. 1}$$

Incremental changes between parameters can be easily calculated by differentiation.

The diffraction efficiency describes optical properties of, the or each, hologram when replayed by incident light, generally of a broad band spectral nature. For example, in a transparent THICK reflection hologram where fringes are tilted, the diffraction efficiency is described by Eqn. 2 below $$\eta = 1/(1 + (1 - (\xi/\nu)^2))/(\text{sech}(\nu^2 - \xi^2)^{0.5})^2 \qquad \text{Eqn. 2}$$

where $$\nu = j \cdot \pi \cdot n_o \cdot t(\lambda \cdot (\cos(\theta) \cdot (\cos(\theta) - \lambda \cdot \cos(\theta f)/n \cdot D))^{0.5}) \qquad \text{Eqn. 3}$$

and where $$\xi = -\Omega t/(2 \cdot (\cos(\theta) - \lambda \cdot \cos(\theta f))/n \cdot D) \qquad \text{Eqn. 4}$$

The dephasing measure denoted by $\Omega$ quantifies deviation from the Bragg condition.

The Modulation Transfer Function (MTF) depends on grain size of the holographic support medium and any modifications made to the spatial detail in the material which forms the hologram.

Bandwidth ($\Delta\lambda$) at a diffraction angle ($\theta$) is due to spacing distribution of fringes throughout the support medium. However, in reality the detected bandwidth is, in addition, a function of a finite range of viewing angles (field of view).

There are at least four basic ways to change a hologram and thereby vary an optical characteristic. A combination of one or more of these may be employed to affect a change in the hologram and/or holographic support medium, so as to give rise to a change in a physical property of the holographic element.

The first technique involves destruction of the structure of the holographic element i.e. spoiling the integrity of the holographic element. Thus the regularity of the structure of the hologram throughout the support medium and modulation depth of the fringes defining the hologram, may be destroyed and the support medium containing fringes may be progressively removed from the holographic element. For example, this can be achieved by enzyme or chemical action which cleaves bonds at specific sites in the gel which forms a structural support matrix of the holographic support medium.

Figure 19:
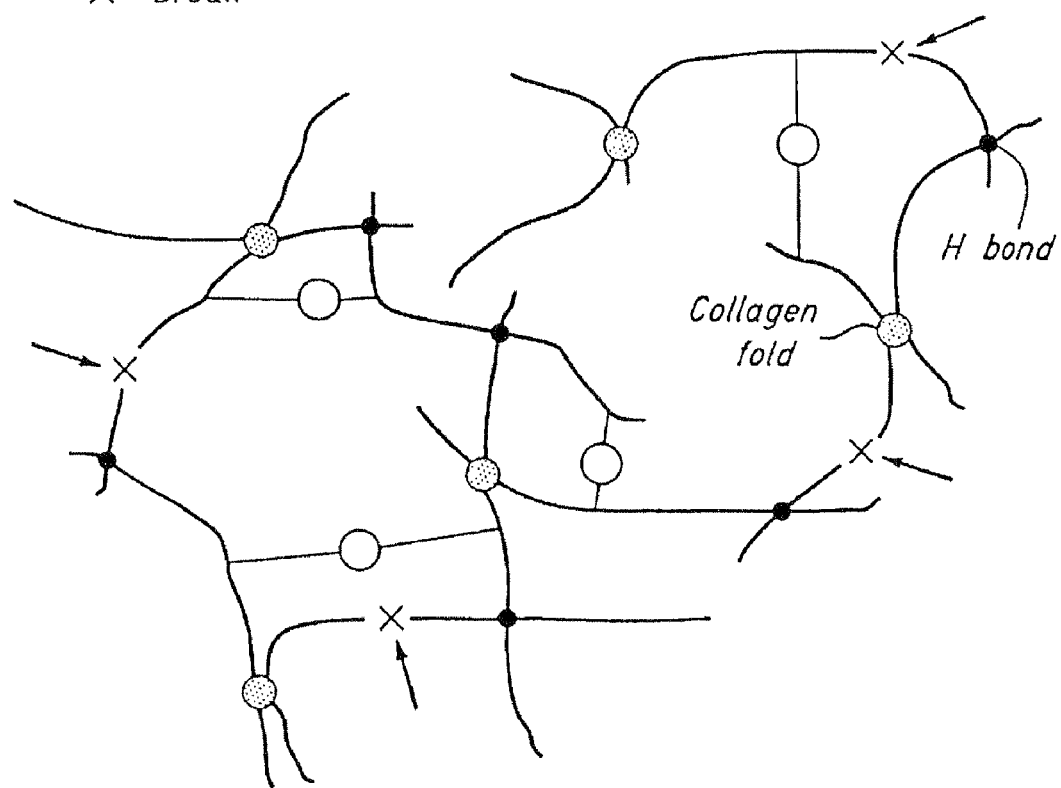
FIG. 19 shows diagrammatically bond destruction occurring in a holographic support medium and illustrates diagrammatically the effect an enzyme has in breaking bonds in gel strands.
Figure 20:
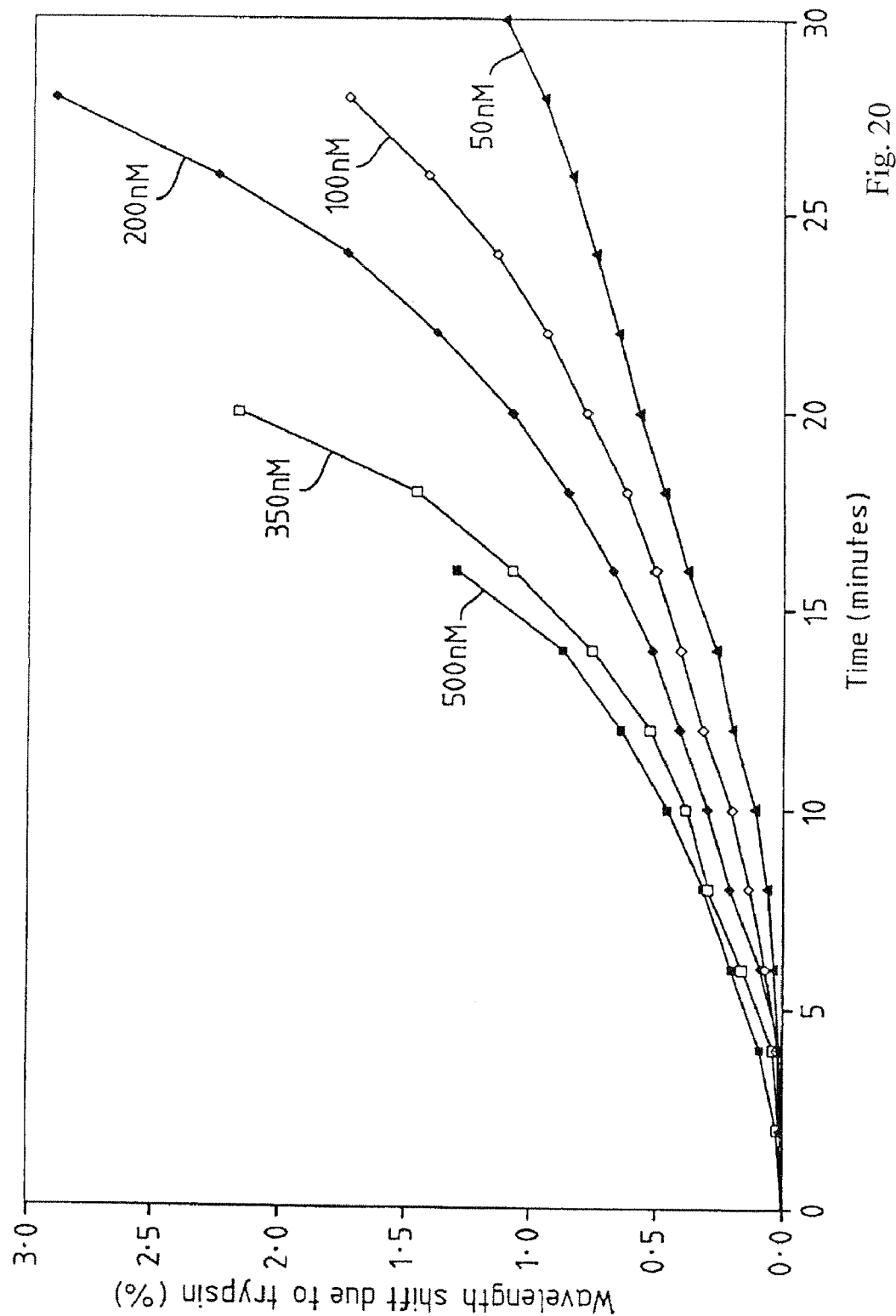
FIG. 20 shows a graph of trypsin action on a reflection hologram showing the rise in reflected peak wavelength, with time, as the support medium is weakened and swells.
Figure 21:
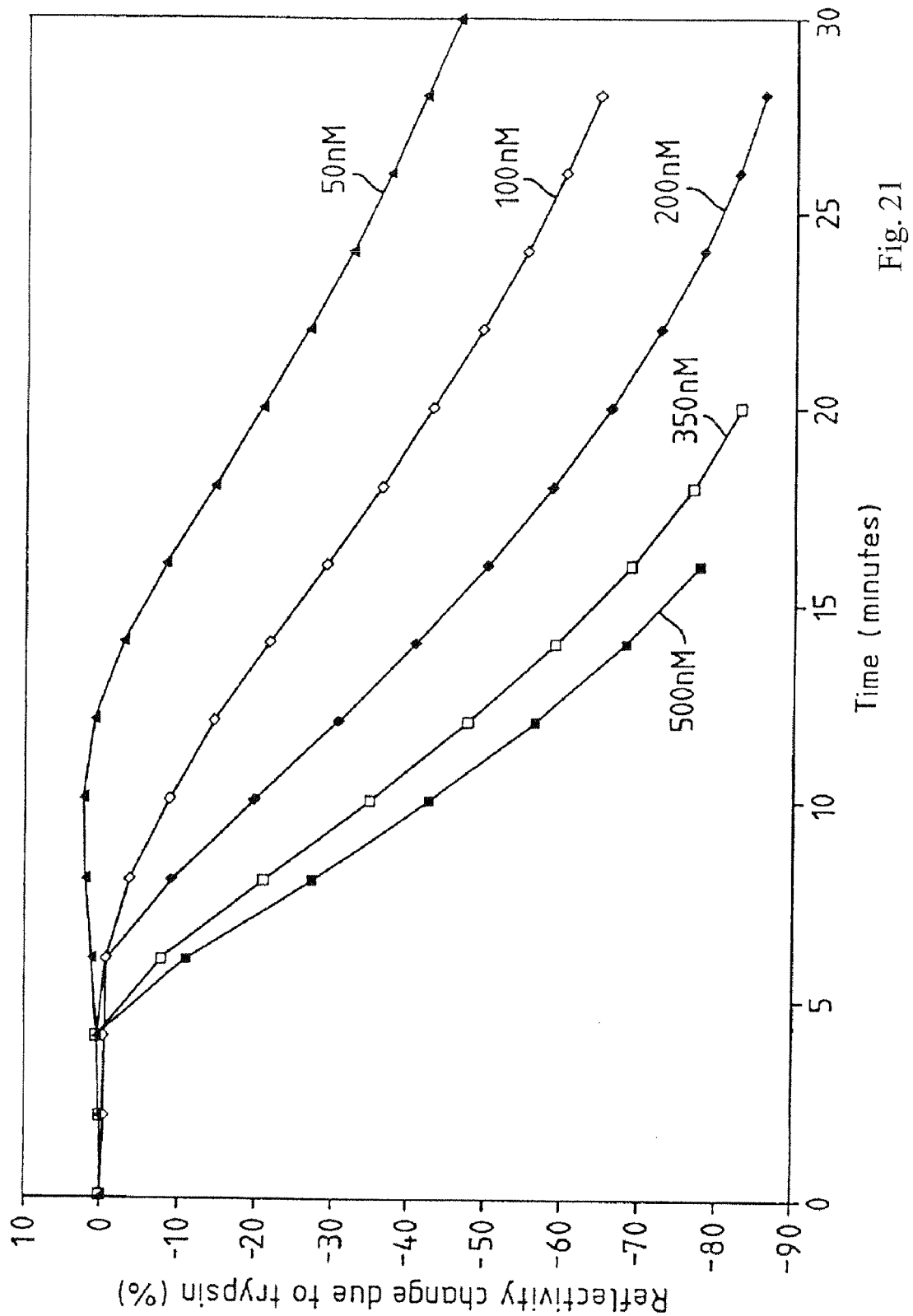
FIG. 21 shows a graph of trypsin action on a reflection hologram showing initial enhancement of diffraction efficiency then loss of diffraction efficiency, measured in a spectrophotometer against time.
Figure 22A:
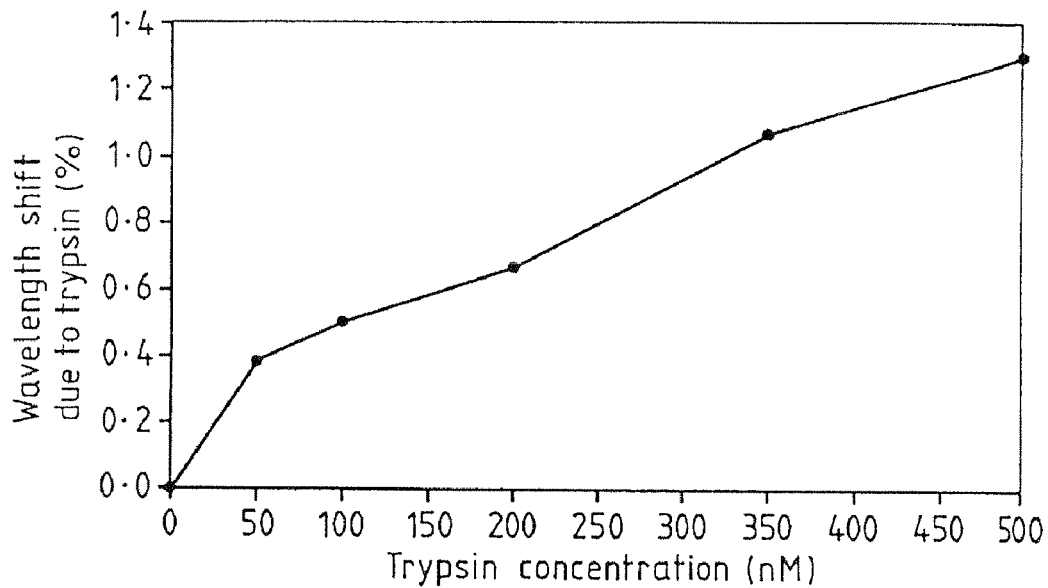
FIG. 22a shows a graph of trypsin action on a reflection hologram showing concentration of trypsin and peak wavelength change at timed intervals.
Figure 22B:
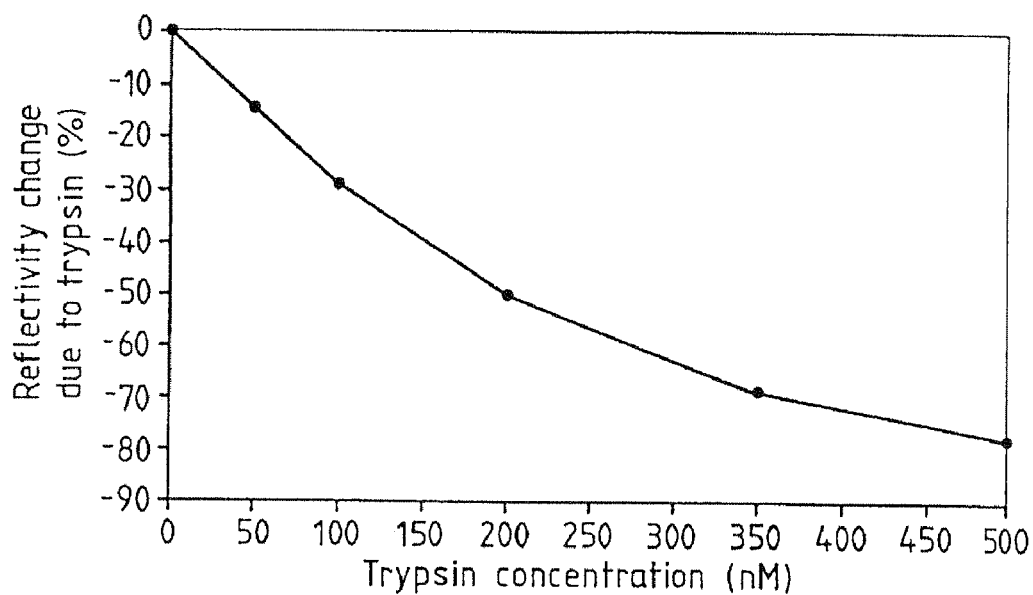
FIG. 22b shows a graph of trypsin action on a reflection hologram showing concentration of trypsin and peak reflectivity change at timed intervals.

FIG. 19 shows, diagrammatically, how the aforementioned phenomenon is realised in principle. For example, trypsin has been shown to act on a gelatin-based hologram so that diffraction efficiency has been changed. FIGS. 21 and 22b show graphs of the results of such an experiment. As is apparent from FIGS. 20, 21 and 22, a hologram of this type may be used as a sensor for enzymes, in that a variation in reflection or transmission of light by a hologram can be used to detect concentration of the protease. A degree of specificity in net optical response (net optical response is the combined optical output of two or more holographic elements) may be provided, for example, by application of an appropriate inhibitor to a control sample and no inhibitor to the sample used in, or on, the holographic support medium and/or hologram. Specificity to an enzyme may also be provided by including the enzyme substrate in the holographic support medium.

The second technique is to change the size of the holographic element in order to change one or more optical properties.

This may be achieved by changing for example, the active water content of the support medium. The holographic support medium preferably comprises a gel. The second technique results in two distinct applications. These are:

2a. Detection of trace levels of water in solvent using a dry support medium or, optionally, gel-based hologram. Trace active water enters the support medium, causing it to expand thereby altering an optical property.

2b. Detection of trace levels of solvent in water using a previously saturated hologram. The solvent reduces the activity of the water so that the volume of the holographic support medium reduces.

Figure 23:
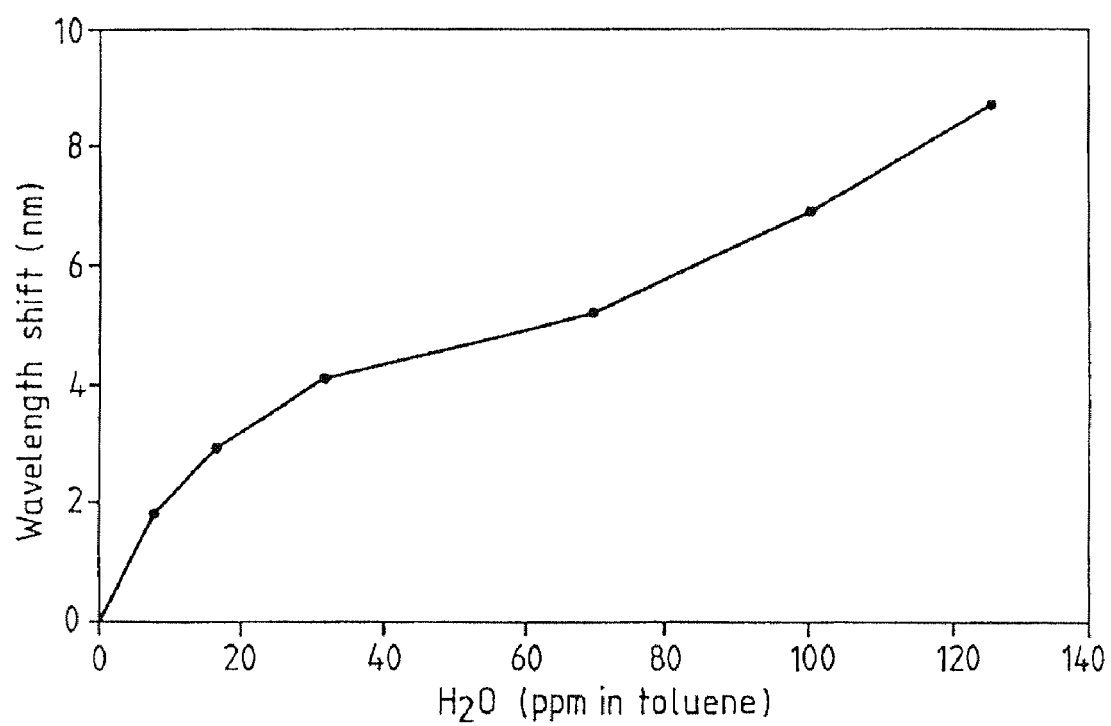
FIG. 23 is a graph showing sensitivity of a reflection hologram to trace water in solvent, using a white light spectrometer at 0° incidence and relates wavelength shift (nm) to ppm water in toluene.
Figure 25:
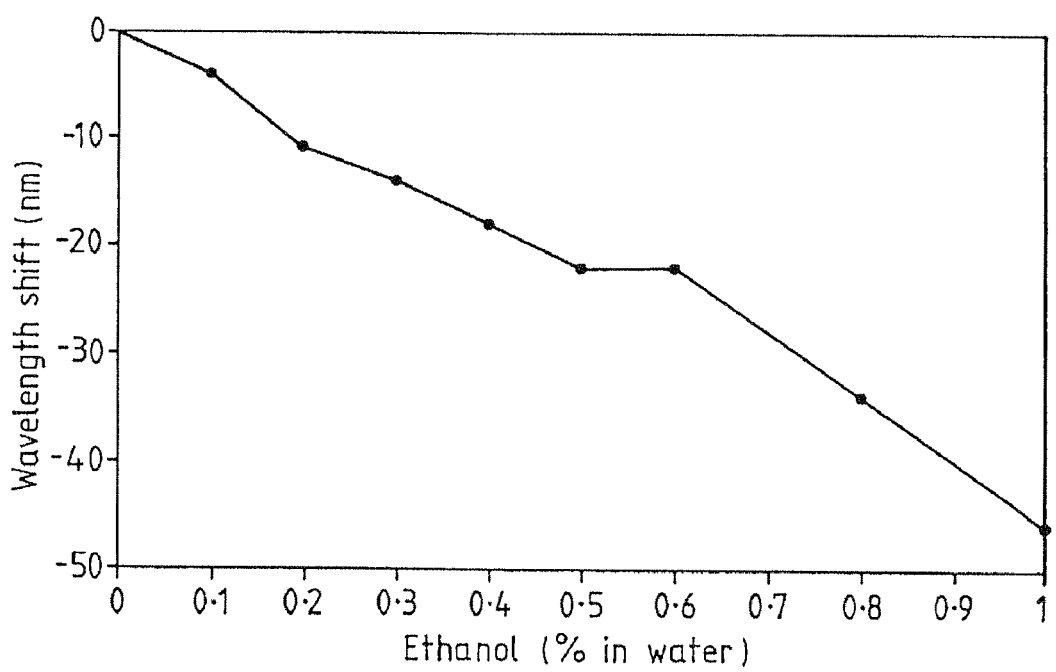
FIG. 25 is a graph showing sensitivity of a reflection hologram to trace ethanol in water using a white light spectrometer at 0° incidence and relates wavelength shift (nm) with concentration of ethanol in water.

Applications 2a and 2b are illustrated by graphs in FIGS. 23 and 25 respectively. FIGS. 23 and 25 show results of a typical experiment. The details of the experiment are described below.

Figure 26:
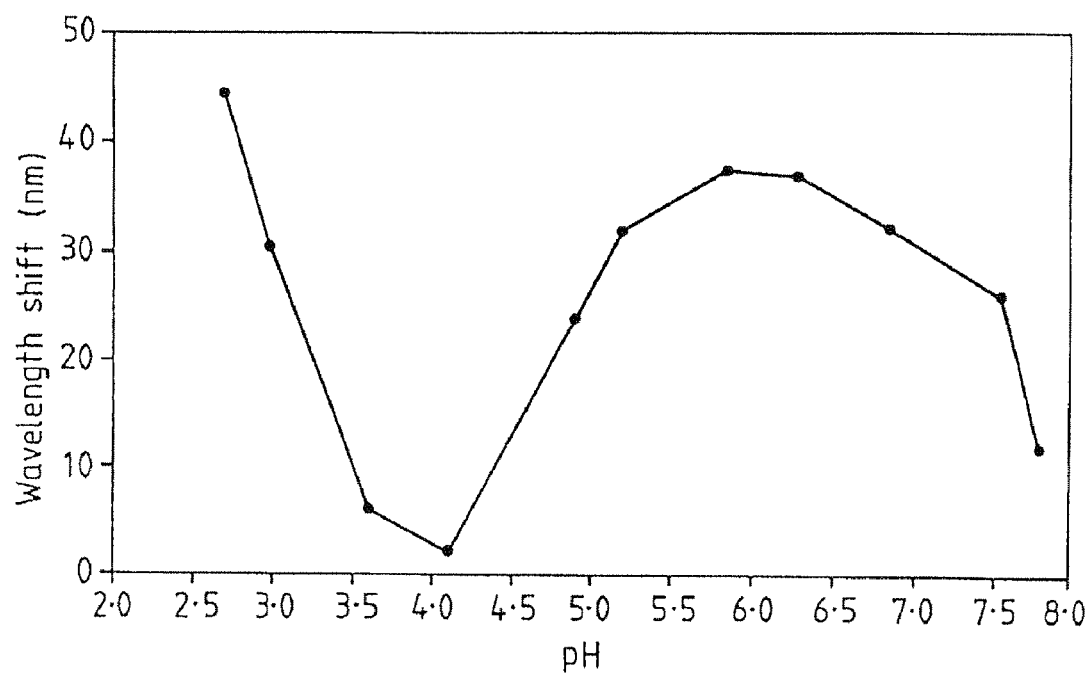
FIG. 26 is a graph showing the effect of pH on a reflection hologram using a white light spectrometer at 0° incidence and relates pH to wavelength (nm) shift.

2c. A further mechanism is to change osmotic forces by, for example, altering the pH, i.e. pH sensitivity. FIG. 26 shows a graph of the result of a further experiment illustrating this while the holographic support medium is saturated with water.

2d. A further mechanism can be one or more in combination of: (a) addition/removal of molecules and bonds; (b) changes in local charge distribution in molecular groups; and (c) conformational changes of molecular structure. When at least one of these occur a change occurs in visco-elastic forces which hold the matrix of the holographic support medium together/apart. When, for example, water is drawn into a dry support matrix, the support matrix (the gel, for example) swells until all forces equilibrate. At this point swelling stops. A strengthening of the visco-elastic forces expels water and the shrinking support matrix causes the separation (D) and angle ($\theta f$) of fringes to decrease. This is shown diagrammatically in FIG. 15b. A weakening of the matrix permits uptake of water and increased fringe separation.

Figure 18A:
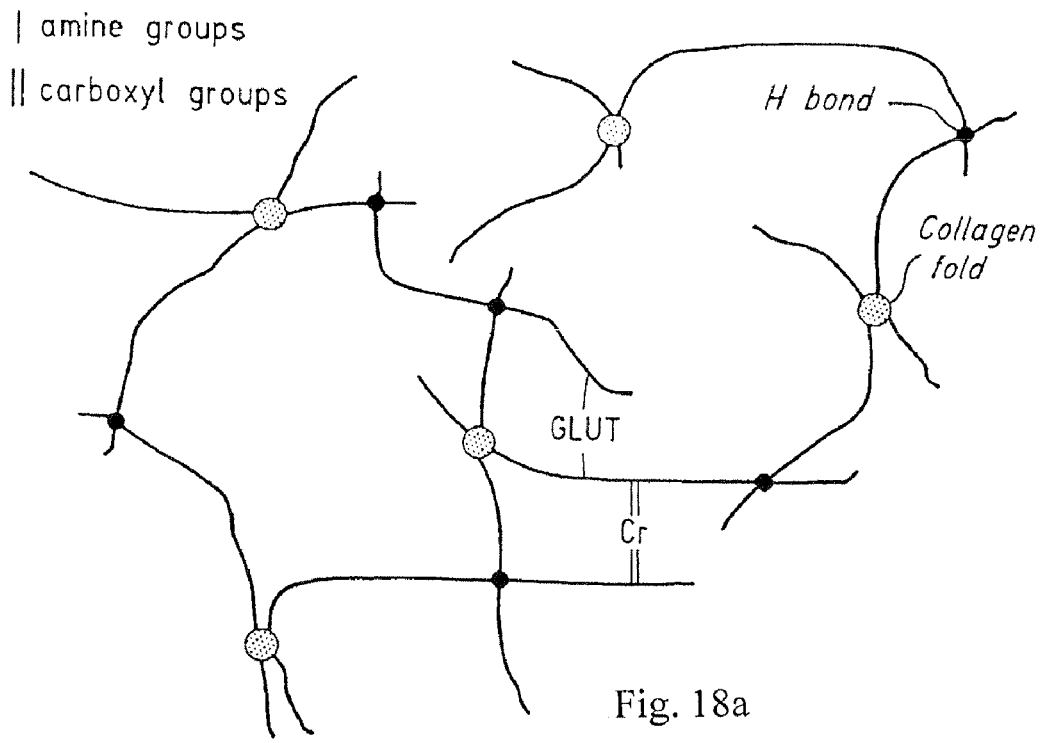
FIGS. 18a to d show diagrammatically bond linking between molecules.
Figure 18B:
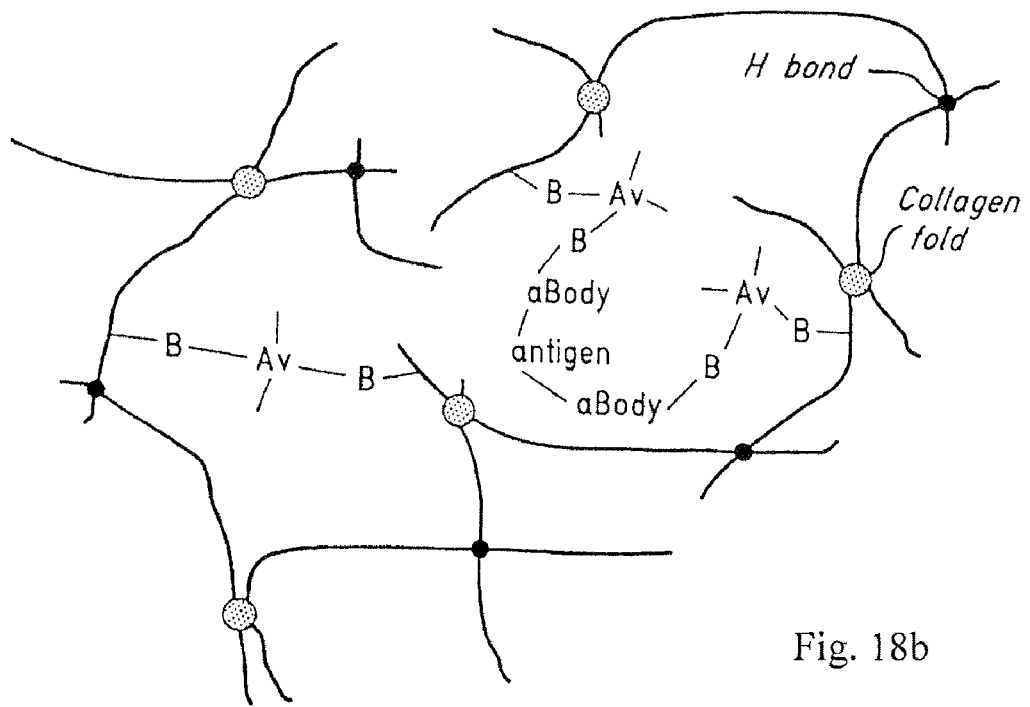
Figure 18C:
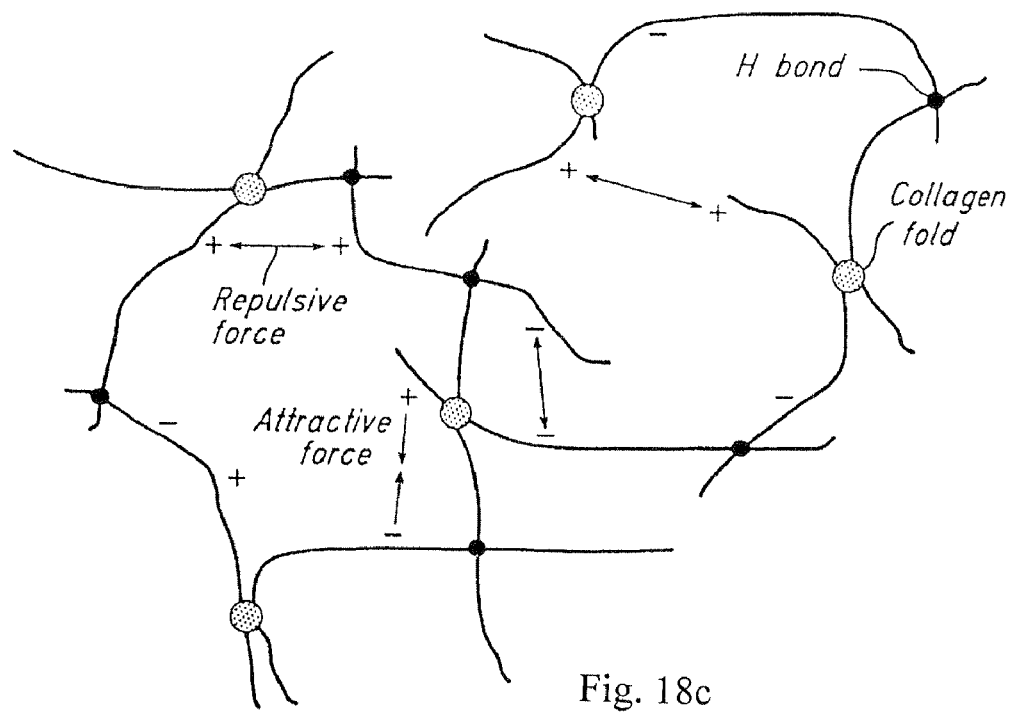
Figure 18D:
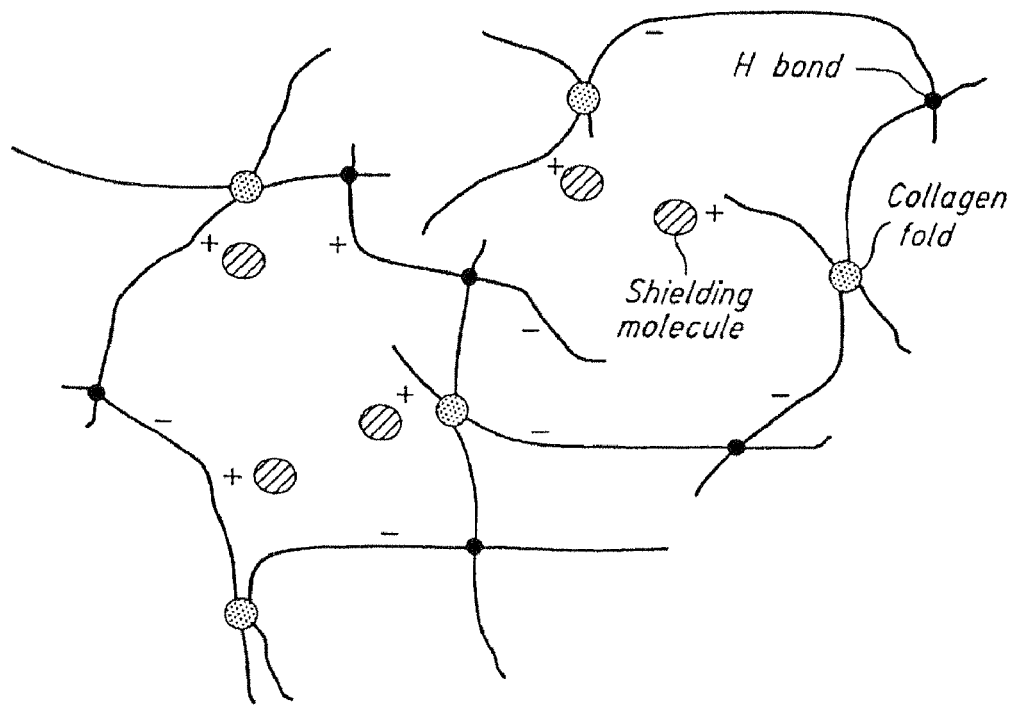

For example, trypsin has been shown to have another effect whereby alteration of charge distribution weakens the support matrix and, subsequently whereby cleavage of peptide bonds in gel strands also weakens the support matrix allowing a saturated gel to swell, increasing fringe separation and therefore the Bragg wavelength of the hologram. FIGS. 20 and 22a show the results of such an experiment. This type of sensor may be used as an immuno-sensor. FIG. 18b shows diagrammatically how this phenomenon may be realised in principle.

The mechanism for modification of the sensor, for example, for use as an immunosensor is such as to ensure the holographic support medium (or holographic element as a whole) is prepared so as to contain a first molecular species which is the specific binding conjugate of an analyte. Analyte molecules, with at least two functional groups or those attached to a label molecule with at least two functional groups, will bind specifically to at least two of the first species so as to form a cross-link between separate parts of the support matrix, thereby altering the visco-elastic properties of the support matrix. Consequently, if present within a water-containing environment, and the support matrix changes, the support matrix contracts and the separation (D) of the fringes is reduced. This change in fringe separation (D) may be measured by peak (Bragg) wavelength change at a fixed angle of incidence/diffraction or by monochromatic intensity change at a fixed angle or by an angle change at monochromatic peak intensity. Specificity in the technique (described above at sub-paragraph 2d) may be provided by ensuring that specific binding sites are provided within the gel matrix.

The third technique is to change the modulation of complex index of refraction by chemical modification of the holographic element, in order to change one or more optical properties. For example, an enzyme can initially enhance the depth of the modulation of complex index of refraction by cleaving at sites in between fringes. This phenomenon is shown for the example of trypsin by the initial gain in total net reflectivity in the low concentration trace of FIG. 21.

Figure 35:
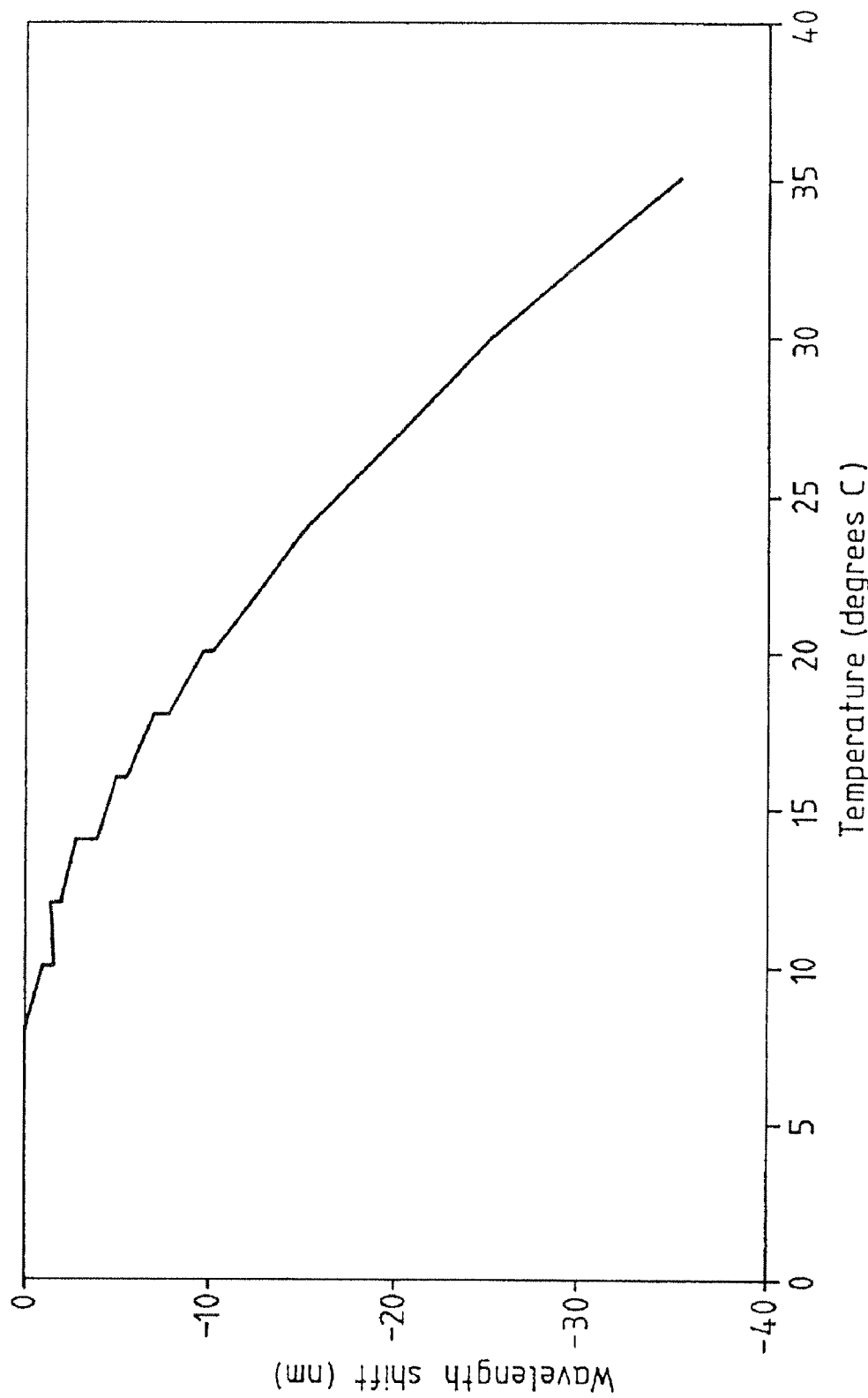
FIG. 35 shows a graph of wavelength shift (nm) against temperature (° C.).

The fourth technique is to prepare the holographic element so that its response to an interaction with an analyte is a temperature change. One or more dimensions of the holographic element, for example, will change as a result of the temperature change. This results in a change in one or more optical properties. Temperature sensitivity of a reflection hologram is shown in FIG. 35.

If any of the four above mentioned mechanisms occur, whilst the hologram is being replayed by incident broad band, non ionising electromagnetic radiation, then an optical property varies and a colour or intensity change, for example, may be observed. Detection is by measuring any of the measurands in TABLE 1 as appropriate to the parameters changed. The nature of the relationships between some parameters and measurands are illustrated in equations 1-4.

Judicious selection of hologram type, fabrication technique and analyte species therefore permits a number of different sensors to be produced. Such sensors may be tailored to detect specific compounds, events or biological species. Their sensitivity may be varied by careful choice of specific binding conjugate, type of hologram and fabrication technique used. Thus a sensor having both quantitative and qualitative sensing properties may be made cheaply and easily.

It is understood that the above mechanisms are not an exhaustive description of the possible mechanisms. Furthermore it is understood that applications described are by way of example only and are not considered to be the only types of application. Examples of support media are described below.

The holographic support medium is one in which a hologram can be made and which is capable of exhibiting one or more of the properties of the sensitive mechanisms described above.

Preferably, the support medium comprises a native or modified matrix with visco-elastic properties which alter as a result of an interaction with an analyte species.

An example of such a material is gelatin which is a standard material used in holography for supporting photosensitive species, such as silver halide grains. Alternatively, gelatin can be photo-cross-linked by chromium III ions, between carboxyl groups on gel strands. Other examples of holographic support media are:

i) K-carageenan.
ii) agar or agarose.
iii) polyvinyl acohol (PVA).
iv) the broad classification of a sol-gel.
v) the broad classification of a hydro-gel.
vi) acrylates.

It will be appreciated that many types of holographic support media exist and the above list is not exhaustive.

Examples of analytes which may be identified and quantified by a sensor of WO-A-95/26499 are:

| | |
|---|---|
| water and specifically water activity | enzymes |
| ions | proteins |
| haptens | gases |
| oligonucleotides | metabolites |
| cells | viruses |
| aldehydes | bacteria |
| formaldehydes | fungi |
| | yeasts |

The aforementioned list of analytes is given by way of example only. Other analyte species may exist and could be identified with a suitable sensor, in accordance with WO-A-95/26499.

In some cases, sensitivity and detection is facilitated by any binding system, where either partner is incorporated into the holographic support medium and the other is the analyte. Examples are:

| | |
|---|---|
| enzyme-substrate | dye-protein |
| ligand-protein | coenzyme-protein |
| carbohydrate-lectin | DNA—DNA |
| DNA-protein | hapten-antibody |
| antigen-antibody | ligand-receptor |
| catalytic systems | enzymes (catalytic antibodies) |
| imprinted polymers | |

Embodiments of WO-A-95/26499 are now described, by way of examples only, with general reference to the Figures and with particular reference to FIGS. 14a to 37b.

Figure 14A:
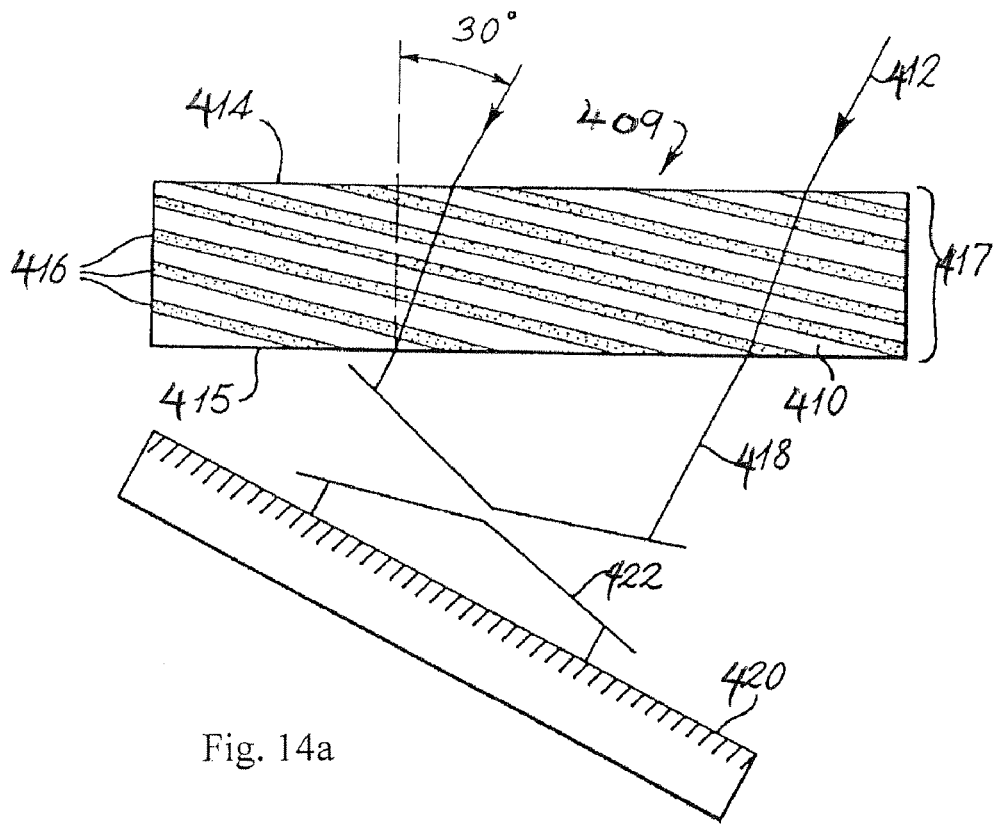
FIG. 14a shows diagrammatically one type of hologram.

Referring to FIG. 14a, a hologram element 409 comprises holographic support medium 410 and modulated complex index of refraction (fringes) 416. Fringes 416 are fabricated as follows: Incident laser light rays 412 impinge surface 414. Laser light rays 418 emerge from the holographic support medium 410 at surface 415 and are reflected off mirror 420. Interference fringes 416, defining hologram 417, are formed when reflected light rays 422 interfere with incident light rays 412. Hologram 417 is thus formed throughout the volume of the holographic support medium 410. In some variants, further chemical processing is required to complete hologram fabrication.

A detailed description of manufacture of the sensor appears below. Reference to standard techniques of emulsion preparation is made as it is considered that the skilled person is familiar with such techniques.

The principles of construction of a hologram are illustrated in FIGS. 14a, 27 and 30. Principles and examples of reconstruction (replay) of a hologram are illustrated in FIGS. 14b, 15, 28, 29 and 31.

Figure 14B:
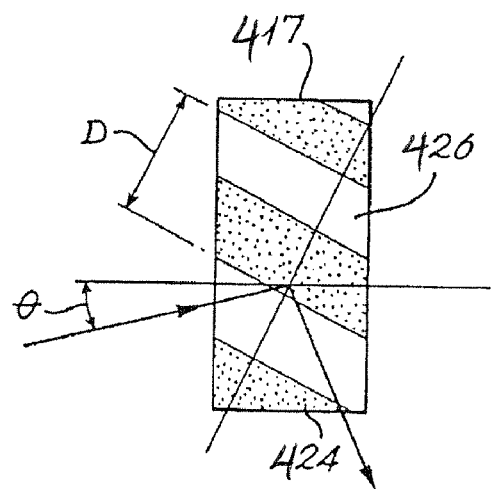
FIG. 14b shows schematic diagrams of fringes, replay rays and associated vectors.

In order to illustrate some of the sensitive detection mechanisms pertaining to a sensor of WO-A-95/26499, brief description is made with general reference to FIG. 14b, of the diffracting and replay properties of a plane wave hologram. Specific mechanisms are described with reference to other Figures.

In general, a hologram 417 is a three-dimensional (3-D) grating which converts incident light into one or more beams having spatial and spectral dependence on the internal parameters of the hologram 417. Typically a grating comprises a refractive index or absorption modulation of the material 424 within a support matrix 426. The material 424 may be an alteration of the support matrix 426 itself. The modulation is referred to as fringes 416 as in FIG. 14a. The hologram 417 itself acts as a transducer element of a sensor if an analyte (not shown) modifies an internal parameter so as to produce a measurable change in an optical property of the hologram 417 when the hologram 417 is reconstructed or replayed.

It will be appreciated that any of the interrelated parameters and measurands shown in TABLE 1 above may be deduced from the effect.

Referring also to FIGS. 14a-b and 15a-b, FIG. 19 shows, diagrammatically, the breakage of bonds (indicated with an "X") in a support matrix 426. This is believed to have two effects; weakening of the matrix 426 permits the matrix to swell (mechanism 2d above) causing fringes 416 to separate further; and Bragg wavelength or angle to increase. The regularity and integrity of the modulated complex index of refraction forming the fringes 416, is perturbed so as to reduce the optical efficiency of the hologram (mechanism 1 above). In extreme cases, material 410 containing fringes 416 is removed so as to reduce the optical efficiency of the hologram.

Referring also to FIGS. 14a-b and 15a-b, FIG. 18b shows, diagrammatically, the addition of molecular cross-links in a matrix 426. Cross-linking may be provided chemically or, more specifically, by reactions between specific pairs of molecular conjugates in a binding system. This has the effect of strengthening the matrix so as to limit the extent to which the matrix can swell (mechanism 2d above). The effect is to limit the fringe separation and therefore the extent of change in Bragg wavelength or angle. If such types of cross-link are removed by whatever reaction, specific or not, then the effect is to weaken the matrix and permit it to swell. Thus the effect is to permit fringe separation and therefore Bragg wavelength to increase or Bragg angle to change accordingly.

Referring also to FIGS. 14a-b and 15a-b, FIGS. 18c and 18d show, diagrammatically, the contribution of electrostatic forces to the strength of the matrix 426 whereby a shielding/revealing or other alterations of charge distribution changes the net strength of the matrix (mechanism 2d above). The effect is to change the size of the matrix, a weakening permitting swelling and a strengthening limiting swelling so that separation of fringes 416 changes accordingly and a corresponding change in Bragg wavelength or angle results. FIGS. 17a-b show how charges present in, for example a gelatin support matrix vary with pH. The graph of FIGS. 16a-b shows how Bragg wavelength changes with pH (mechanisms 2c and 2d).

Other mechanisms (2a and 2b above) relate to water activity in an originally-dry and originally-saturated matrix 426 respectively. In either case water activity causes a change in the equilibrium size of the matrix 426 and FIGS. 14a-b and 15a-b illustrate how the Bragg condition is altered.

Reference is now made to particular applications of the sensor. In a particular example, the change in peak reflectivity and wavelength at fixed incident angle were measured and calibrated against trypsin concentration. Graphs of the results appear at FIGS. 22a and 22b respectively. It is readily apparent that a sensor may therefore be fabricated whose characteristics are predictable and which may be used to correlate intensity or colour of a light signal to concentration or action of proteolytic enzyme. In the example shown, the matrix which supports the hologram is gelatin, a convenient substrate for proteolytic enzymes. It is apparent that a sensor for other enzymes will be made in a support matrix containing a corresponding substrate. For example, a sensor for amylase would include a starch component in its support matrix. Furthermore, the utilisation of enzyme action can be extended to a specific system, an immunosensor, for example, where the selected enzyme is used as a label attached to an antigen bound to an antibody which is immobilised in a secondary layer above a holographic element containing the enzyme substrate. Upon exposure to antigen analyte, competitive binding releases the enzyme-labelled antigen which diffuses into the holographic element where the enzyme degrades the support matrix. Holographic optical response is a result of analyte antigen concentration and activity.

A further application is in sensing bacteria such as *bacillus* and pseudomonas, for example, whereby secretion of proteolytic enzymes has the above effect on a gelatin hologram, for example.

An application of a cuvette-based embodiment is for measuring water activity in solvent or reagent. For example, water in toluene has been measured down to a concentration level below the typical detection limit of an existing standard test called the Karl-Fischer method (K.F. test). The parameter changed in this case was fringe spacing and is detected as a peak intensity colour change at a fixed angle. FIG. 23 shows results obtained using the holographic sensor.

Another application of the aforementioned embodiment is measuring solvent levels in water. For example, ethanol in water was measured down to 0.1%. Again, the parameter changed is fringe spacing and is detected as a peak intensity colour change at a fixed angle. FIG. 25 shows the result obtained using the holographic sensor.

Another application of the sensor is in formaldehyde sensing, employing the aforementioned cross-linking mechanism whereby formaldehyde cross-links, for example, gelatin, pulling the gelatin molecules together thereby causing the support medium to shrink and the Bragg wavelength to reduce. This may be achieved in a matrix which has not been previously hardened via the amine groups so it is advantageous to the performance of the device to use a customised holographic support medium.

Reference is now made to particular embodiments of the sensor. It will be appreciated that these are by way of example only and variations to the embodiments described will not depart from the scope of the invention.

Embodiments of the invention incorporated into sensor systems are now described, by way of example only, and with reference to FIGS. 28a-b, 29, 31, 32, 33 and 34, in which like parts bear the same reference numerals. The Figures show a holographic element 432 on a mechanical substrate 433. The separation or angle of the fringes (not shown) is varied, or the refractive properties of the holographic element 432 is changed causing an optical response to a variety of analytes, specifically or not, depending on their identity and on the preparative treatment given to the element 432. The identity of the analytes depends further on which of the aforementioned mechanisms are employed. The embodiments are now described.

Figure 15A:
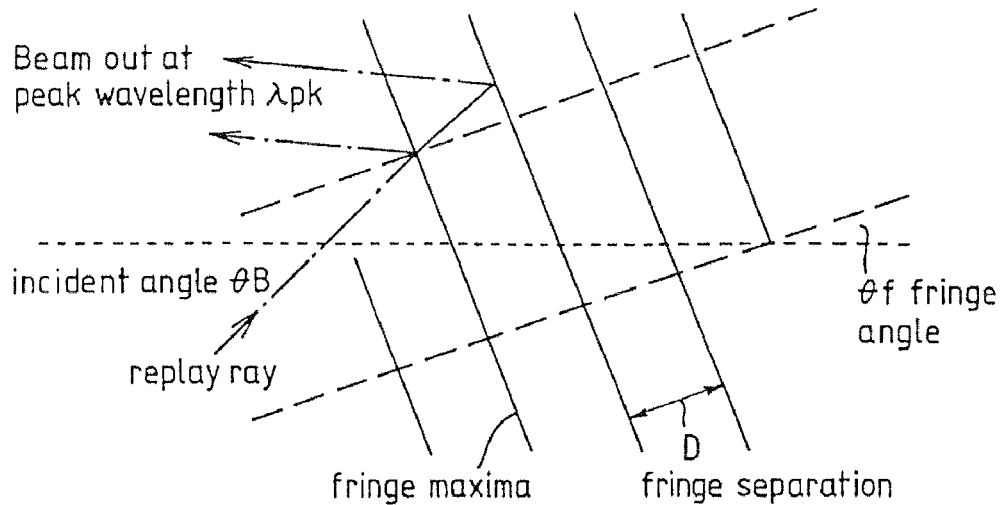
FIG. 15a shows diagrammatically some of the optical parameters referred to in TABLE 1, with reference to a ray diagram of a thick reflection hologram.
Figure 15B:
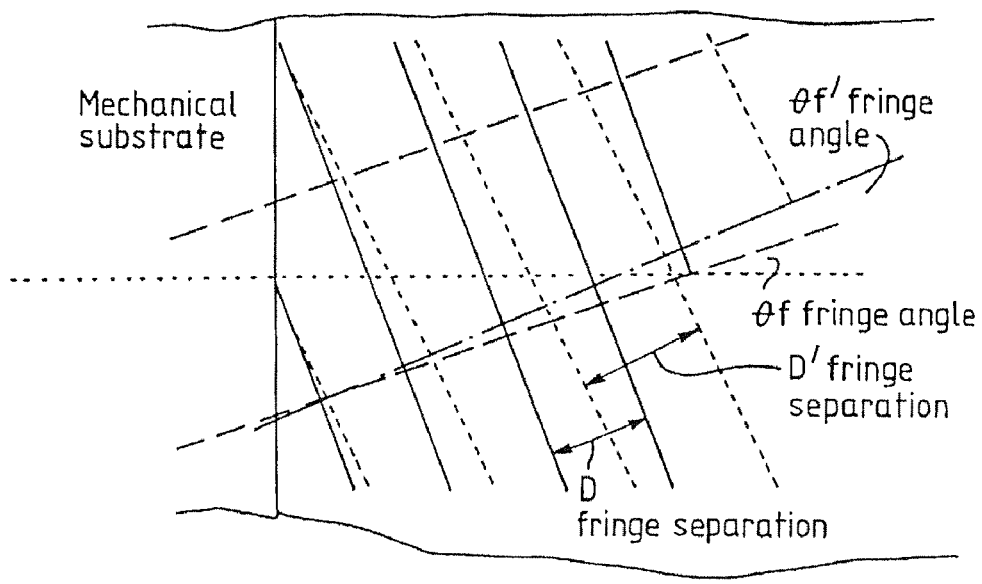
FIG. 15b shows fringe angle and separation change which occurs when there is hologram swelling.

An embodiment of the invention is incorporated into a sensor system, and is shown in FIG. 15a-b. The sensor comprises a holographic element 432 supported on substrate 433 inside a container 439 which may be a spectroscopic or a fluorometric cuvette. The change in spectral response shown diagrammatically in FIG. 28b, to an appropriate analyte is measured via a standard spectrophotometer (not shown).

Another embodiment of the invention is incorporated into another sensor system, and is shown in FIG. 29. The sensor comprises holographic elements 32a and 32b, representing test and reference sensors respectively, where 32a and 32b are contained within a container of a liquid or gas which in turn contains an analyte. Response is visualised directly as a colour or intensity change.

Figure 31:
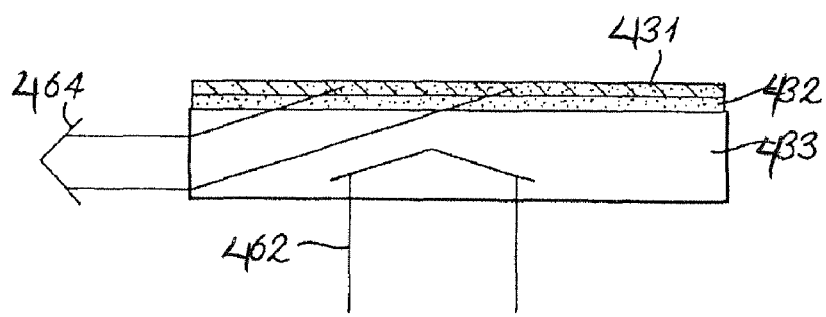
FIG. 31 shows diagrammatically replay of an "evanescent-wave hologram" as embodied in a sensor.

Another embodiment of the invention may be incorporated into a sensor system, shown in FIG. 31. The sensor comprises a holographic element 432, comprising a hologram 431 in a support medium, illuminated by light 462 which can be of a narrow or broad-band nature. The changing intensity and/or spectral response 464 of hologram 431, to an analyte, is monitored by a photodiode (not shown) or spectral processor (not shown) or by direct visualisation.

Figure 32:
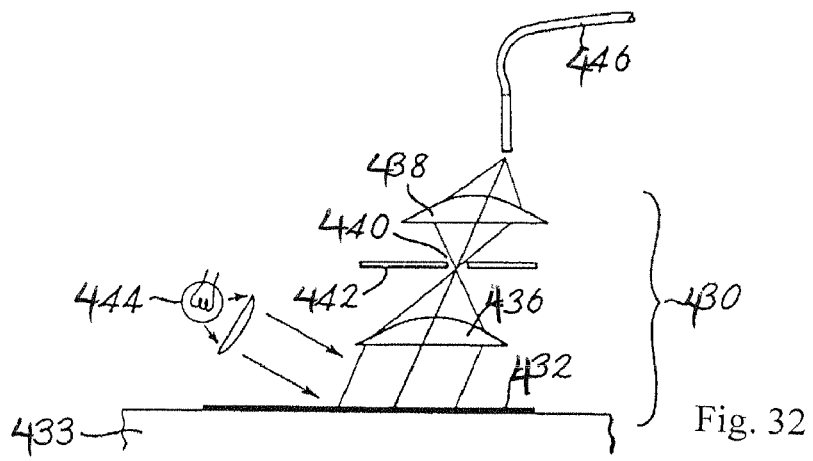
FIG. 32 shows a fibre optic array acting as a hologram reader, at fixed viewing angle (but whole-spectrum illumination), for use in conjunction with a sensor.

Another embodiment of the invention may be incorporated into another sensor system, shown in FIG. 32. The sensor comprises a holographic element 432, an arrangement of lenses 436 and 438 together with a narrow aperture 440 in a suitably opaque material 442 to ensure that light from a broad-band source 444 is directed within a narrowly-defined angle of incidence to a fibre optic 446. A wavelength shift or intensity change in light reflected from 432 can be visualised as a colour or intensity change at the end of a fibre optic 446 or it can be processed by suitable electronic or spectrographic means (not shown).

Figure 33:
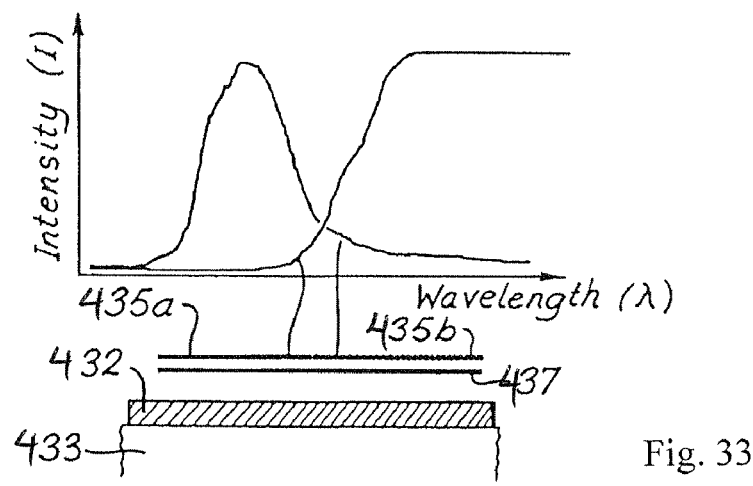
FIG. 33 shows an example of a filtered visual display relying on a wavelength shift for use as a sensor.

Another embodiment of the invention is incorporated into a sensor system, and is described with reference to FIG. 33. The sensor comprises a holographic element 432, a message mask 437, a high-pass filter 35a and a low pass filter 35b. Passbands are also shown on the sketch of the graph of Intensity (I) against wavelength. A spectral change in the passband of the hologram in 432 as a result of an analyte interaction is visualised directly as a change from a positive to a negative indication or vice-versa.

Figure 34:
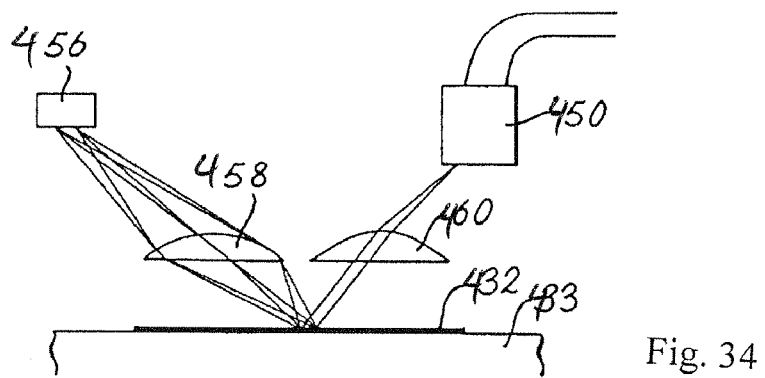
FIG. 34 shows a fibre optic array hologram reader and holographic sensor, having a fixed wavelength but a varying Bragg angle.

Another embodiment of the invention is incorporated into a sensor shown in FIG. 34. The sensor system comprises an appropriate holographic element 433 supporting a hologram 432, a monochromatic light source 456, a lens 458, providing a range of angles incident onto the hologram 432, and lens 460 for focusing light onto a linear array of fibre optics 450. A change induced in the hologram 432 changes the Bragg angle which can be visualised or otherwise detected at the end of the fibre optic 450. A linear photodetector array (not shown) may be employed directly in place of the fibre array as an angle detector.

Figure 36A:
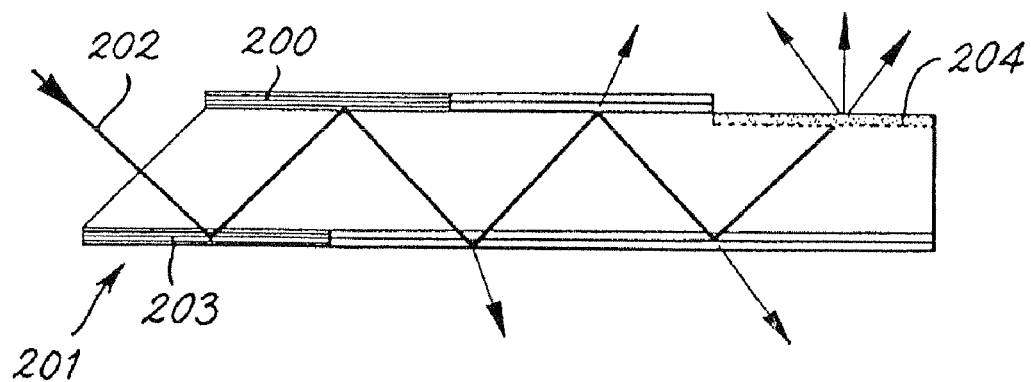
FIG. 36a shows a diagrammatical view of a holographic sensor with a reference, incorporated into a dipstick format.
Figure 36B:
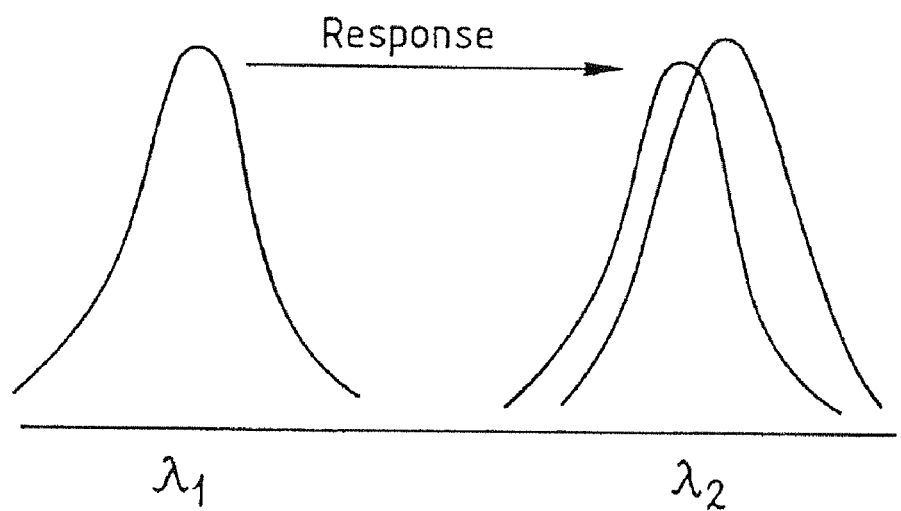
FIG. 36b shows graphs of spectral shift of output signal from a reference hologram with respect to a sensor hologram.
Figure 37A:
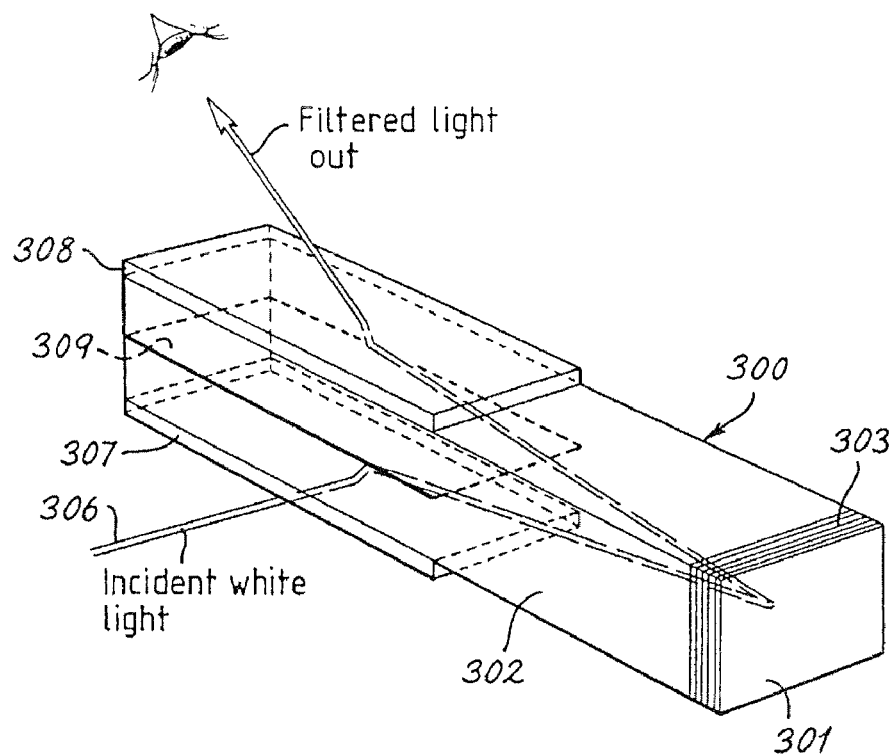
FIGS. 37a and 37b show diagramatically another embodiment of a dipstick incorporating a specific holographic sensor and a spatially-varying indicator.
Figure 37B:
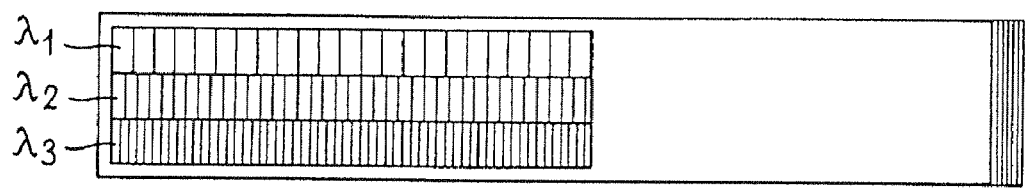

Another embodiment of the invention is incorporated into a sensor shown in FIG. 36a. The sensor comprises a first (reference) holographic element 200 supporting a hologram ($\lambda 1$), situated on a clear transparent bar or dipstick 201 shaped so that light can enter the dipstick at one end 202, thereby illuminating a test holographic element ($\lambda 2$) 203. Light is reflected at and around the Bragg wavelength within a narrowly defined range of angles so that it is incident upon the holographic element 200 which acts as a reference. The second holographic element 203 is different from the first holographic element 200 in that it will not respond to the specific analyte and in that its passband is at a longer wavelength. As long as no analyte is present then the Bragg wavelengths of the two holograms 200 and 203 do not match and light will not reach a message mask 204. When analyte is present then light is transferred along the dipstick 201 (which acts as a light pipe) and to the illuminated message mask 204 which indicates a positive response. Non-specific effects alter the two passbands equivalently. The lightpath geometry is arranged to restrict the range of angles transmitted in order to improve response discrimination. FIG. 36b illustrates diagramatically the relative spectral shift of incident light.

Another embodiment of the invention is incorporated into a sensor system 300 shown in FIGS. 24a and b. The sensor system 300 comprises an appropriate sensitive holographic element supporting a hologram 301, situated at one end of a transparent bar or dipstick 302 and at least one further holographic element 303, not sensitive to analyte. All three elements are arranged so that light path 306 is defined as shown. Side elements 307 and 308 couple light into and out of the bar respectively. More than one holographic element may be arranged in parallel adjacent strips each with a different Bragg response so that the response from each sensitive holographic element is visually apparent as a spatial change as well as a colour change. This is shown diagramatically as $\lambda 1$, $\lambda 2$ and $\lambda 3$ in FIG. 37b. An opaque screen 309 acts as a light blocker and is placed between transparent windows 307 and 308.

One particularly useful and readily achievable application of the sensor, as described in any of the aforementioned embodiments, is as a water sensor. The water sensor can be easily and conveniently manufactured. A method of manufacturing the water sensor comprising a holographic sensor is described below.

The ability to easily measure the lowest residual water content of many substances, that are generally considered to be "dry", is of great importance in many branches of industry and science. For example the water content of liquid hydrocarbons, alcohols, or ethers are routinely carried out so that chemical or biological reactions can be performed with these substances. For more than fifty years the common method used for measuring water content has been that published by Karl Fischer (KF) in 1935. This method is essentially one of titration. A non-aqueous solution of elemental iodine is added dropwise from a burette into an aliquot of substance whose water content is required to be known. The substance has to have added to it the sulphite of an amine such as pyridine whose water content has to be predetermined and allowed for. The elemental iodine and the sulphite ions attack any water molecules present to produce sulphate and iodide ions. The "end point" occurs when no more water is available and an excess of unreacted iodine appears in the aliquot.

There are a number of disadvantages in this method. Solutions require precalibration, they have a limited shelf life; and they impose handling restrictions and the need for carrying out the titrations under a fume hood.

A holographic sensor of WO-A-95/26499 requires only a small test strip of holographic grating to be immersed in the liquid, solid, solid-in-suspension or gas whose water content is required to be known. After a short period, typically about 10 minutes of mild agitation, to achieve homogeneity in the medium immediately surrounding the grating, the water content can be ascertained from the change in colour of the grating when it is illuminated (replayed) under a white light source. The colour change can be compared with a calibrated test chart, preferably of holographic form by the naked eye or examined using a spectroscope.

The aforementioned holographic water sensor has been found capable of measuring water content from 0.01% to 100% to within experimental error. The method of preparing the holographic grating however has to take into account whether it is to be used to measure in the lowest or highest range. The acceptable range of expansion/contraction of the grating from its original size is limited by broadening and peak reduction of the response peak as the grating "mark/space ratio" departs from unity. The mark/space ratio describes the spatial distribution of refractive index that defines the grating. Methods of construction of both gratings are described below. The method used for the lowest water levels is described first in relation to measuring trace water in solvents.

The preparation and use is now described.

A Lippmann emulsion is first coated onto a glass sheet. A typical method such as that based on the description by H. Thiry in Journal of Photographic Science, Vol. 35, 1987 may be used. The finished and dried emulsion is then exposed to monochromatic light in the simplest type of set-up to produce a holographic grating similar to that shown in FIGS. 14a and 14b. In a preferred arrangement a plane mirror reflects light through the emulsion along the normal so that it interferes with incident light to form a standing wave grating with fringes half a wavelength apart. This type of grating after processing and cutting into suitably sized strips, is intended for use in a sample cell of a spectrophotometer cuvette, for example of the type shown in FIGS. 27 and 28a. A blank reference cell cuvette (not shown) consists of the same dried emulsion as in the sample cell but this strip has been exposed to white incoherent light so it does not contain a grating and by being given the same processing treatment, any intrinsic colour bias in the film is the same in the reference cell as in the sample cell as is known by a skilled person. The grating is positioned in the spectrophotometer cuvette's sample cell with its emulsion facing towards the liquid. The cuvette may need to be capped tightly to keep out atmospheric moisture. The replay wavelength is able to be monitored because the grating reflects it back along the same axis as the specularly reflected light and therefore it registers as an absorption process. As the grating absorbs moisture from the sample liquid, considerable wavelength shift can occur due to the swelling effect. The wavelength shift is dependent on the moisture uptake by the gelatin. Unlike the usual manner in which measurements are made by a spectrophotometer, the peak height is not of direct relevance.

FIG. 23 shows the sensitivity of such a sensor when used to measure water in samples of toluene that were specially prepared from extremely dry toluene, spiked with very small quantities of water. All the solutions were prepared and extracted under dry nitrogen using septum caps and syringes with fine needles. The ordinate shows absorption maxima of the spectrophotometer beam in nanometres. In the case of particularly hydrophobic substances such as toluene, the sensitivity of the sensor can be about 10 times greater than could be achieved with the Karl Fischer detection method. However, in the case of a very hydrophilic substance such as iso-propyl alcohol (IPA) the sensitivity is apparently about the same as in the Karl Fischer (KF) method.

One reason for this difference in sensitivity depending on the degree of hydrophilicity of the sample, can be explained as follows: hydrophilic groups in the polypeptide chains in the gelatin of the holographic sensor, attract water mainly through the hydrogen bonding processes. Therefore these groups have to compete with the hydrogen bonding process which gives the high affinity for water shown by, for example, iso-propyl alcohol. This results in the hologram only swelling to some equilibrium value, whereas in the case of toluene such competitive hydrogen-bonding does not occur. In the KF system the bonding energy obtained through sulphite changing to sulphate, probably means that the reaction with water is virtually fully complete in both hydrophobic and hydrophilic solvents. Therefore the KF system may be said to measure water content, whereas the holographic sensor could be said to measure water "activity". This feature gives the holographic sensor an additional advantage over the KF system when measuring water in solvents which are being used for biocatalysed reactions. In these cases it is the water activity rather than the total water content which is significant.

Figure 24:
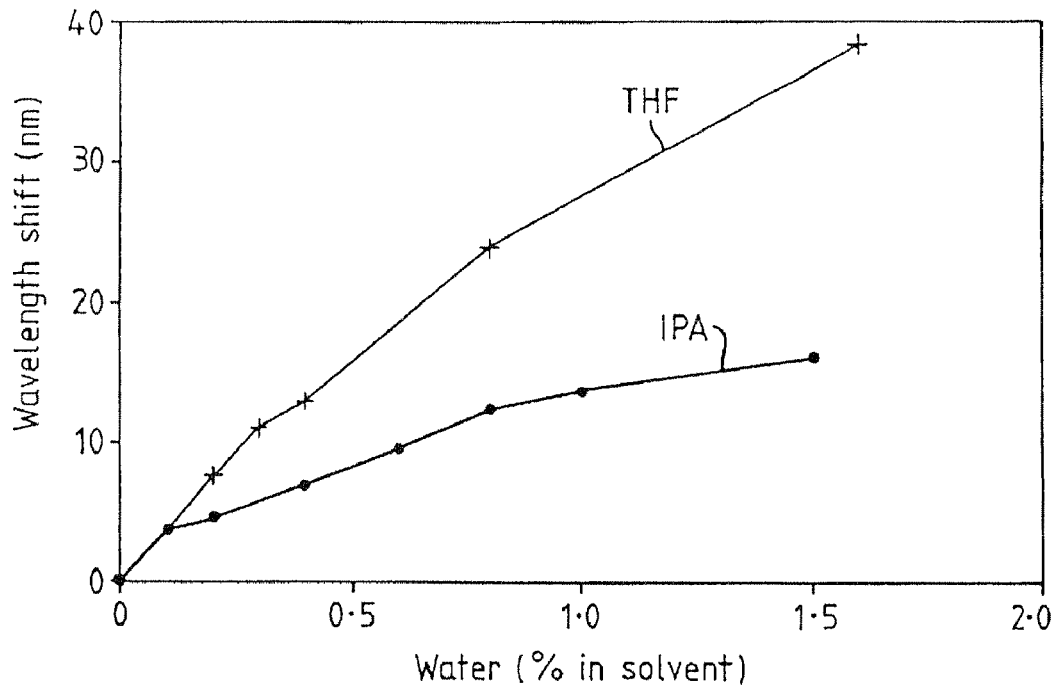
FIG. 24 is a graph showing sensitivity of a reflection hologram to trace water in solvents (IPA and THF) with different hydrophilicity.

FIG. 24 shows results obtained with holographic sensors used to measure the water content of both IPA and THF (tetrahydrofuran). The lower hydrophilicity of THF can be seen to cause a steeper slope (higher sensitivity) than in the case of IPA. All tests were conducted at a temperature of 25° C.

The following example describes the preparation and use of a "label-based" hologram for general sensing of water in solvents.

A particularly useful feature of the sensor is that it enables very low levels of water contamination in for example, an organic solvent to be readily detectable by the naked eye and be sufficiently inexpensive to be able to be marketed, for example, as a disposable strip or label stuck to the inside of bottles of organic solvent. A technique is described below.

A grating was exposed as shown in FIG. 14a but with the monochromatic light 412 source inclined at about 30 degrees to the normal. The hologram 417 was developed and bleached in a standard manner. The purpose of making the grating off axis by about 30 degrees was to enable diffracted light not to be obscured by specularly reflected light off glass or plastic support surfaces (not shown). Two identical 1×0.5 cm strips of grating were cut out and each one was stuck to the inside wall of a 500 cc glass bottle near the base, with the emulsion side facing into the liquid. The bottles were then thoroughly dried for a half hour at 70° C. in a drying oven. Each of the two bottles were then filled with 330 cc. of anhydrous toluene and a small magnetic stirrer bar and then sealed with rubber septum caps to keep out atmospheric moisture. The bottles were positioned on a magnetic stirrer so that each one displayed an identical diffracted image of an overhead white strip light. To an observer the image of the strip light looked yellow. 50 microliters (0.050 cc) of pure water was then injected into just one of the bottles and both bottles were stirred for about 30 minutes. When both bottles were placed side by side in a suitable viewing position of the grating, it was evident that the bottle that had been contaminated with water displayed an orange coloured grating whereas the other still displayed a yellow grating. The water content of the spiked toluene was 150 ppm. The lowest water content measurable by a typical KF system is around 1000 ppm. Therefore even without using a spectrophotometer an assessment was made by the naked eye with the holographic sensor which exceeds what is possible with a typical KF system.

The embodiment described in the aforementioned test is shown diagrammatically in FIG. 29. The holographic grating is subdivided so that a protected area of the strip can act as a control so that comparison can be made on the exposed area affected by moisture.

A sensor is fabricated for detecting water, in a gas flow. A thin strip of grating equilibrated in an ambient relative humidity of 60%, replays an orange colour under a white light source. The sensor is then placed in a transparent glass tube attached to tubing from a supply of dry nitrogen gas. A small burst of nitrogen gas causes a rapid change of colour of the grating from orange to turquoise. The effect appears almost instantaneous. Intermediate levels of humidity may be achieved by first bubbling the gas through various concentrations of sulphuric acid in a gas bubbler or Dreschel bottle. Intermediate colours between turquoise and orange can be seen in the grating and changes are so rapid that no independent means were available to verify the actual relative humidity changes in the tubing.

A hologram suitable for use at high water activity will now be described.

To use a holographic sensor in an aqueous environment as, for example, in measuring trace solvent in water, it may be necessary to make one alteration to the exposure arrangement shown in FIGS. 14a and 14b. The holographic support medium should be in a swollen state when the exposure to monochromatic light is made. This swelling is achieved by exposing the material while it is immersed in an aqueous solution. The reason for this is to achieve visible replay when the hologram is in the swollen state. FIG. 25 shows the effect of adding ethanol to pure water. This measures the lowering of water activity, i.e. the degree of hydrogen bonding between the gelatin of the grating and the water is reduced by competition from the hydrophilic organic solvent and hence swelling of the grating is reduced.

TRYPSIN EXAMPLES

A useful application of the sensor is as a sensor for the proteolytic enzyme trypsin, particularly in neonatal screening for cystic fibrosis and detection and monitoring of pancreatic disorders in general. An example of a method describing a holographic sensor for this type of application appears below.

Trypsin is produced by the pancreas and secreted into the human digestive system. Its identification is an indicator of pancreatic exocrine function. An important example of trypsin detection in medicine is in screening for cystic fibrosis during the neonatal period when elevated (by a factor of two or three) levels of blood immunoreactive trypsin or reduced levels of intestinal trypsin give a positive response to the condition. It is important to identify the disease as soon as possible in order that treatment of the secondary pathology can commence. There are a few screening methods, the most reliable and specific of which is an expensive and time consuming radioimmunoassay for blood trypsin. Only those tests which prove positive are followed-up by a relatively low cost test for elevated levels of sodium and chloride ions in sweat.

A simple test for trypsin in stool samples is based on the destructive action of the enzyme on the gelatin layer of an X-ray film. The end point is defined as the dilution of the stool at which the dissolution of the film is not visually observed. The test is not specific or quantitative.

The response of a gelatin-based reflection hologram to trypsin has been shown as a function of nominal concentration down to 50 nM in, FIGS. 22 a-b. Duodenal trypsin is normally likely to be in the range 250 nM to 3000 nM. It is therefore possible to calibrate such a device to give a quantitative indication of trypsin concentration. Improvement to the device tested can be obtained by softening the gelatin to obtain greater sensitivity and by making a thinner film to obtain an even faster response.

The holographic sensor described when applied to trypsin, provides a faster. cheaper and quantitative alternative to existing tests.

In one preferred embodiment, a sample of stool or duodenal fluid is applied to the test hologram which is replayed via an optical path which is preferably situated away from the sample site. Preferably, the illuminating source is a light emitting diode and the detector is a photodiode so that a measurement of intensity is interpreted as trypsin concentration using low-cost readily available electronic processing equipment.

A reference hologram, pre-treated with trypsin inhibitor, provides a correction for interfering components in the sample.

In another preferred embodiment, the test hologram is made in a support medium which consists, in total or in part, of substrate material specific to trypsin i.e. containing predominantly lysine or arginine functional groups.

Figure 30A:
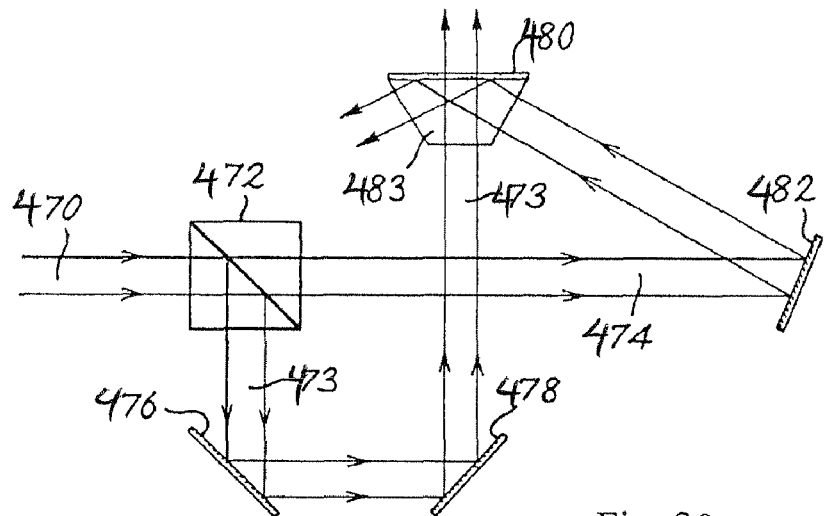
FIGS. 30a and 30b show diagrammatically thin hologram construction using an evanescent wave as one of the interfering beams.
Figure 30B:
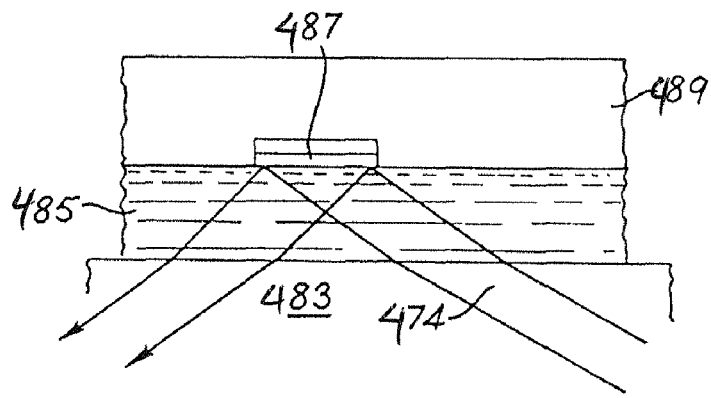

A preferred hologram type is an edge-lit, thin hologram, as described previously, created using interference between one or more evanescent light beams and one or more evanescent or homogeneous beams. These terms are familiar to one skilled in the field of optics and holography. The method by which an evanescent wave hologram may be made is illustrated in FIGS. 30a-b. FIG. 30a shows an illuminating beam 70, from a Helium-Neon (HeNe) laser, passing through a beam splitter 472. Beam 473 is reflected off mirrors 476 and 478 and impinges with surface of a holographic film 480. Beam 474 is reflected off mirror 482 and interferes with beam 473 after passing through a high index prism 483. The hologram formed is shown in diagrammatic detail in FIG. 30b. High index liquid 485 allows total internal reflectron at its interface with the film 480. An evanescent region 487 is defined in emulsion 489. The operation of the edge-lit hologram thereby created is described below, with reference to FIG. 31. An advantage of the edge-lit type shown in FIG. 31 is that the optical path 464 can be conveniently defined for location of the illuminating source 462 and the detector. The evanescent wave technique typically provides a hologram of around half a wavelength thickness so that speed and extent of response due to penetration and effect of analyte is improved.

As presented above, WO-A-95/26499 describes, in a general manner, constructing and using a sensor, such as the sensor of the present invention.

Alternatively, the sensor of the present invention may be constructed and used in the manner generally described in WO-A-99/63408, which provides a chemical sensor that addresses the need for an alternative method of production of silver halide-based holographic recording material. This is achieved by using a sequential treatment technique similar to that described by Talbot, where the polymer film is made first, and the sensitive silver halide particles are added subsequently. This approach is combined with materials that have not previously before used for holographic recording.

According to a first aspect of WO-A-99/63408, a method for preparing a holographic sensor of the type wherein the holographic recording material forming the analyte-sensitive element is a non-rigid polymer matrix, comprises diffusing soluble salts into the matrix where they react to form an insoluble light-sensitive precipitate with a particle size less than the wavelength of light; a holographic image may then be recorded.

This method can be used to produce volume holograms, of the general type disclosed in WO-A-9526499, suitable for use as sensors. The polymer matrix may be gelatin, but an advantage over the prior art is that other, better defined polymers can also be used. For example, the matrix may be an insoluble polymer film. The matrix may have any of the following advantageous characteristics (many of which are distinct from those of gelatin):

a defined pore volume specific for the analyte or a component thereof;

hydrophobicity;

homogeneity;

inertness with respect to any material reactive with gelatin;

non-charged;

requires processing, during or after formation, that is incompatible with the presence of the photosensitive substance; cannot stabilise silver halide colloids in solution;

has a structure comprising essentially only regular repeating units.

According to a further aspect of WO-A-99/63408, a sensor for an analyte comprises a hologram supported on or within an insoluble polymer film, wherein at least one optical characteristic of the hologram varies as a result of variation of a physical property occurring throughout the bulk of the matrix.

A sensor according to WO-A-99/63408 preferably uses as its support a transparent glass or plastics substrate which has been pre-treated or "subbed" to improve the adhesion of the overlying polymer layer which will support the holographic structure. The nature of the pre-treatment depends on the substrate material and the polymer that will overlay it. Many techniques are known to those skilled in the art, including silanisation of glass and U.V., thermal or chemical bonding of thin polymer layers to the surface. The most appropriate method is chosen for the combination of materials being used.

A film of the polymer of interest for a particular sensing application is then deposited on top of the pre-treated substrate. The polymer is typically any that has a regular structure of the type comprising, say, at least 50 or 100 repeating units of the same basic structure in the primary chain, whether a homopolymer or copolymer. Typical polymers for use in a sensor, according to WO-A-99/63408, are selected from polyvinyl alcohol, polyvinylpyrrolidone, polyhydroxyethyl acrylate, polyhydroxyethyl methacrylate, polyacrylamides, polylmethacrylamides, homopolymers or copolymers of polymerisable derivatives of crown ethers, and esters of or co- or terpolymers of polyhydroxyethyl acrylate, polyhydroxyethyl methacrylate, polymethacrylamide or polyacrylamide, optionally with other polymerizable monomers or cross-linkers.

The polymer may be soluble or insoluble. If soluble, it may be deposited as a film by any of the techniques known for this purpose, such as spin-coating, roller-coating or use of metering rods or doctor blades. The polymer solution used for coating may have chemical cross-linking agents included, in order to render the resulting film tough and insoluble after curing, or the dried film may subsequently be immersed in a bath of a cross-linking agent to render it insoluble. A typical example of this procedure comprises coating an aqueous polyvinyl alcohol (PVA) solution containing a small amount of glutaraldehyde and a trace of acid catalyst to make a stable cross-linked PVA film.

In an alternative approach to making the polymer film, a mixture of appropriate polymerisable monomers can be mixed with thermal, U.V. or visible light initiators and optionally with solvents, and polymerised in situ on top of the substrate. Typical examples of this approach utilise co- or ter-polymers of acrylate, methacrylate or acrylamide-based monomers, preferably mixed with a certain amount of cross-linker to give a stable insoluble film capable of supporting a holographic structure within it.

Regardless of the film formation method, and after appropriate curing procedures, a stable polymer film can be obtained, that adheres to the substrate. The dry thickness of the film is typically 5 to 50 µm, although it could be thicker or thinner if appropriate.

After film formation, the film is optionally washed with a suitable solvent to remove any soluble residues, and may be subjected to further chemical derivatisation steps if appropriate, before proceeding with the incorporation of the photo-sensitive silver halide particles and construction of the holographic structure within the film.

The polymer film is preferably soaked in a solution of a silver salt. This is typically at a concentration of 0.1 to 0.5M. The solvent used depends on the hydrophobicity of the polymer film. For hydrophilic films, aqueous silver nitrate can be used, but, for more hydrophobic materials, solutions of organic soluble silver salts such as silver perchlorate in solvents such as propan-1-ol give much more efficient penetration into the film and hence better silver density in the resulting holograms. The soaking time depends on the nature of the polymer film and can range from less than a minute to hours.

After soaking in a silver salt, the film is optionally dried. The film is then dipped in a bath containing a halide ion. This and subsequent steps must be carried out under safe lighting. By choice, the halide salt is sodium bromide, but chloride or iodide or a mixture, or lithium or potassium salts, may also be used. A sensitising dye matched to the wavelength of the laser that will be used to record the holograms may be also included in the, say, bromide bath. This can be omitted and the hologram sensitised by a post-treatment in a dye solution, but the photo-sensitivity is generally better if the dye is included with the bromide. The bromide bath is preferably agitated, in order to minimise surface build-up of precipitated silver halide.

Immersion time in the bromide bath is very dependent on material. For some polymers, such as polyacrylamide, the time may be very short, e.g. 15-30 seconds. For most materials, a few minutes is optimal, but some materials require longer. The bromide bath can also optionally contain methanol or another water-miscible solvent. In this case, it will usually be necessary to substitute LiBr for NaBr for solubility reasons. The solvent aids penetration of bromide ions into some types of polymer films such as those made from poly (HEMA).

The order of adding the silver salt and the halide salt to the polymer film can be reversed without significant changes to the results. The order described is preferred because it minimises the amount of expensive silver salts involved.

After removal from the bromide bath, the film is washed in water to remove soluble ions and is then exposed to laser light in an appropriate optical configuration. The film can be exposed wet or dry or in any partially swollen state, depending on the final application and the desired reflection colour of the hologram. The degree of swelling during exposure can be used to tune the colour. The holographic exposure can be made using any of the configurations known to those skilled in the art, but a preferred format is a simple reflection hologram made using a plane mirror as the object.

Following exposure, the hologram is developed using an appropriate developer. This can be selected from the wide range of formulations used in holography. For some materials (particularly more hydrophobic ones), a developer containing methanol gives superior results. After development, the film is washed thoroughly with water.

In most cases, it is desirable to fix the developed hologram to remove residual silver halide. This is most conveniently achieved using sodium thiosulphate solution, with the optional addition of alcohol for more hydrophobic materials. Fixing typically requires about 5 minutes but depends on the nature and thickness of the polymer film.

Finally, the hologram may optionally be bleached. Bleaching makes the hologram near-transparent and is helpful if the transmitted spectrum is measured rather than the reflected spectrum. Appropriate bleaching conditions can be chosen from the range of options familiar to those skilled in holography. The preferred configuration for the novel holographic sensors is to use them in reflection measurements. In this case, it is preferable to leave the holograms unbleached since they are more light-stable in this state.

The completed hologram can be used in any appropriate monitoring format. This could be a transmission or reflection spectrometer device, a dip-stick, a fibre-optic probe or a label. These are given by way of example only.

The design of the polymer material from which the hologram is constructed is the key to the analyte-selective sensing abilities of the final device. Many different design approaches could be applied depending on the target analyte and a few will be described here by way of example, although the scope of WO-A-99/63408 should be understood to be very broad and is not limited only to the approaches described below.

One approach is to make the hologram in a natural or synthetic polymer, or a mixture containing one or more such polymer(s), which can be degraded by an enzyme or a group of related enzymes. When the enzyme hydrolyses the polymer, the structural integrity of the polymer film is undermined, and the reflection spectrum of the hologram changes giving a signal. Example 1 (below) describes this approach, using starch to select for an enzyme, α-amylase, which specifically degrades starch chains. By replacing the starch with other carbohydrates, the selectivity would be altered. Thus dextran holograms would select for dextranase and pullulan holograms would select for pullunases and iso-amylases. By using other types of polymers, other classes of enzymes may be targeted, such as proteases.

It is not necessary for the whole of the polymer structure to be degradable by the target enzyme. Only occasional linkages along the main chain of the polymer need to be cleavable, or alternatively, cross-linking sites can be targeted. Example 5 (below) shows how cleavage of the cross-links in a gel structure leads to a signal. This simple chemical example can be extended by designing more complex cross-links, such as ones with peptide spacers containing cleavage sites for specific proteases. These designed synthetic polymer films may thus have specificity for particular proteases.

By coupling short peptide protease substrates to the polymer chains of the film, it may also be possible to create a response by a charge change mechanism. For instance, if the peptide was initially uncharged but created an immobilised charged group when cleaved by the protease, the increase in immobilised charge groups may cause the film to swell, hence generating a response. The converse situation, where a charged group is removed by enzymic cleavage, could also be exploited. In this case, a contraction would be observed. This concept can also be extended to other classes of enzymes using appropriately designed substrates.

The design concepts for holographic sensors are not limited to systems using cleavage mechanisms. If the analyte of interest changes the microenvironment around a particular type of polymer chain, it may cause the polymer chain to change its conformation, leading to a measurable volume change. This is demonstrated by Example 2 (below), where addition of ethanol to a poly(HEMA)-based hologram causes a progressive swelling which can be used to quantitate the amount of ethanol present.

By inclusion of a specific molecular receptor in the polymer structure, volume changes can be induced upon binding of the molecule in question. This is demonstrated in Example 3 (below) where crown ethers are used as receptors that can specifically bind certain types of metal ions. The response can arise by various mechanisms. Osmotic swelling may occur if charged groups are held in the gel by the receptor. Alternatively, if binding of the analyte causes dimerisation of the receptor, this will tend to pull the receptors closer together and cause a contraction of the film. Binding of the analyte in the molecular receptor may also cause twisting of the polymer chains or otherwise alter the local microenvironment within the polymer film such that a measurable volume change results. Materials such as crown ethers may provide a defined pore volume within which specific analytes are received.

More complex polymer materials may also be designed, where the structure is, at least in part, held together by an interaction between an immobilised analyte and a molecular receptor for that analyte. This generates physical cross-links in the polymer structure. Upon introduction of free soluble analyte, this will compete with the immobilised analyte for the binding sites in the molecular receptor, leading to a reduction in the physical cross-linking of the film and consequently to swelling. This approach may be used with a range of materials and analytes, particularly for antigen/antibody interactions, ligand/binding protein interactions (e.g. glucose with concanavalin A), and interactions of designed artificial receptors with analytes.

For realisation of the many designed materials that could be created for measuring particular analytes, the in situ polymerisation approach described above is preferred, because of the ability to control and design the properties of the resulting polymer film. Specially designed immobilised substrates, receptor molecules, cross-linkers etc. can easily be synthesised and incorporated into films by copolymerisation with other suitable monomers. The degree of swelling can be controlled by alteration of the concentrations of monomers or cross-linkers in the system; hence the behaviour of a hologram can be fine-tuned to match the application, for example with respect to sensitivity and dynamic range. This approach is demonstrated in Example 4 (below), where the pH range over which the sensor operates and the size of the sensor response to a given pH change are both controlled by altering the amount and nature of the ionising species incorporated into the polymer film. Although the in situ polymerisation method is preferable in many cases, other techniques are appropriate for some materials and the scope of WO-A-99/63408 is not limited to this approach.

The following Examples further illustrate a sensor according to WO-A-99/63408.

Example 1

An Amylase Sensor

Starch gratings have the potential to be used as biosensors to detect the concentration of the digestive enzyme alpha-amylase in a body fluid. This can be vitally important as an indication of acute pancreatitis. However starch does not lend itself to the production of ultra-fine grain photographic emulsion when using the conventional technique with gelatin, because it causes severe grain growth before the gelation occurs.

Five steps are described for preparing and using the sensor. These are:
1. The treatment of glass to take a starch coating.
2. The preparation and coating of a layer of starch.
3. The introduction of a light-sensitive fine grain silver halide deposit in the pre-coated starch layer by a diffusion process.
4. Exposure and development to record an optical hologram.
5. Use of the starch hologram as a sensor for amylase.

Step 1

Presubbing Coating:
Solution A
50 ml deionised (DI) water
0.6 g potato starch hydrolysed for electrophoresis (Sigma)
0.6 g Agarose Type A 0169 (Sigma)
The powdered carbohydrates are added to the cold water and stirred on a heater until the temperature reaches about 90° C. The mixture then becomes clear and free of any solid powder.

Solution B
0.10 g ammonium dichromate crystals
10 ml DI water
Solution B is added to Solution A to form a solution for a spin coating.

Clean microscope slide glass is then put in a standard laboratory spin coater and about 1 ml of the solution is pipetted onto the centre of the slide. The spin rate is adjusted to give a thickness of no more than 1 μm. The lighting conditions during this part of the operation should be yellow or free of blue light.

The coating is thin, since a thicker layer may later cause a significant amount of holographic grating to be created in the sublayer. This would then create spurious diffraction effects which might be confused with the diffraction from the starch overlayer which should always be substantially thicker than the sublayer.

The spin-coated material is dry within a minute or even a few seconds. Such spun coated slides are then exposed to a source of strong ultraviolet light for a time sufficient to cause all the ammonium dichromate in the film to crosslink the starch/agarose mix onto the glass slide. It is particularly important that the UV or violet light first passes through the glass side rather than through the film surface.

Step 2

2.0 g potato starch hydrolysed for electrophoresis (Sigma) and 24 g water are heated to 90° C. and stirred until clear. 1.0 ml 10% glutaric dialdehyde solution is added after the solution has cooled to about 50° C.

A relatively thick layer of coating is required on the subbed slides. A number of the subbed slides were lined up without gaps on a horizontal surface and a warmed wire-wound Meyer bar is used (7 turns of wire per centimeter) to govern the coating thickness. The coating is then dried in a tepid air flow and the dry coating is heated at 116 C. for 1 hour, to obtain the necessary degree of crosslinking to enable a stable holographic grating to be formed after the treatment detailed below.

Step 3

Approx 1 ml of a 0.25M solution of silver nitrate is placed on a clean flat surface and a starch-coated slide is pressed face down onto the droplet. The solution then covers the starch coating by surface tension. The solution is left to soak into the starch layer for 2 minutes. It is then removed, and surface liquid on the slide is removed by using filter paper as blotting paper. The slide is then dried for a minute in a strong warm air flow.

36 g lithium bromide is stirred until dissolved in 900 ml water. This is poured into 0.10 g sensitising dye that has been stirred into and dissolved in 300 ml methanol, in a 2 liter beaker and the solution is given a rapid rotation with a magnetic stirrer. The dried slide is held in the rotated solution for a certain time. For convenience this time will be called t(Br); depending on the conditions, its value may be changed.

The starch coating is successfully impregnated with silver halide (in this case AgBr) if t(Br) is 1 minute. If t(Br) is too long, then grain growth can become a problem, but if t(Br) is too short, then the penetration can be insufficient to obtain a later satisfactory gratin. After removing the slide from the bromide bath, it is at once washed under running water.

If the dye is 1,1-diethyl-2,2'-cyanine iodide, then the slide will be sensitized for exposure to a frequency-doubled YAG laser at 532 nm wavelength. If the dye is pinacyanol bromide, then the slide will be sensitized to the 633 nm red from a HeNe laser. The dye does not have to be in the solution of bromide ion at this point but may instead be used in a separate bath after the precipitation of silver bromide has taken place within the coated layer. However, by including the dye in the bromide ion bath, it causes a high light-sensitivity which has been found not to be so achievable if the dye bath is used separately.

The lithium bromide salt may be fully or partially replaced by equimolar equivalents of other halides (not fluorides) such as LiCl or LiI. This will produce various alterations of the nature of the precipitated silver salt within the body of the coated layer. Also, in this particular example, all the lithium bromide may be replaced by sodium bromide.

Step 4

The object used to make the hologram is a plain or curved mirror. The starch-coated plate, preferably in a swollen state, is placed close to the mirror and a diverged laser beam is passed through the coating so that it hits the mirror and is then reflected back through the coating, thus causing an interference pattern in the form of standing waves. This is recorded as a volume hologram with the interference fringes running roughly parallel to the plane of the film (like pages in a book). This principle is well known to those familiar with holographic practices.

After exposure of the slide to the holographic recording conditions, preferably under water or other suitable liquid, the hologram is developed in standard developers such as those detailed in Practical Holography by Graham Saxby, published by Prentice Hall. The development can be stopped by a 10% aqueous solution of acetic acid. Undeveloped silver halide can then be removed in a 15% Hypo solution.

Step 5

The finished, processed and washed grating is cut to fit in a spectrophotometer cuvette. The liquid or sample to be tested for amylase content is added to the tube which should also contain appropriate buffers to facilitate the enzyme reaction on the starch grating. The speed of attack at a given temperature is then monitored by recording one of the characteristic changes to the reflection spectrum of the hologram as a function of time. This can be related to the concentration of amylase in the original sample.

Figure 38:
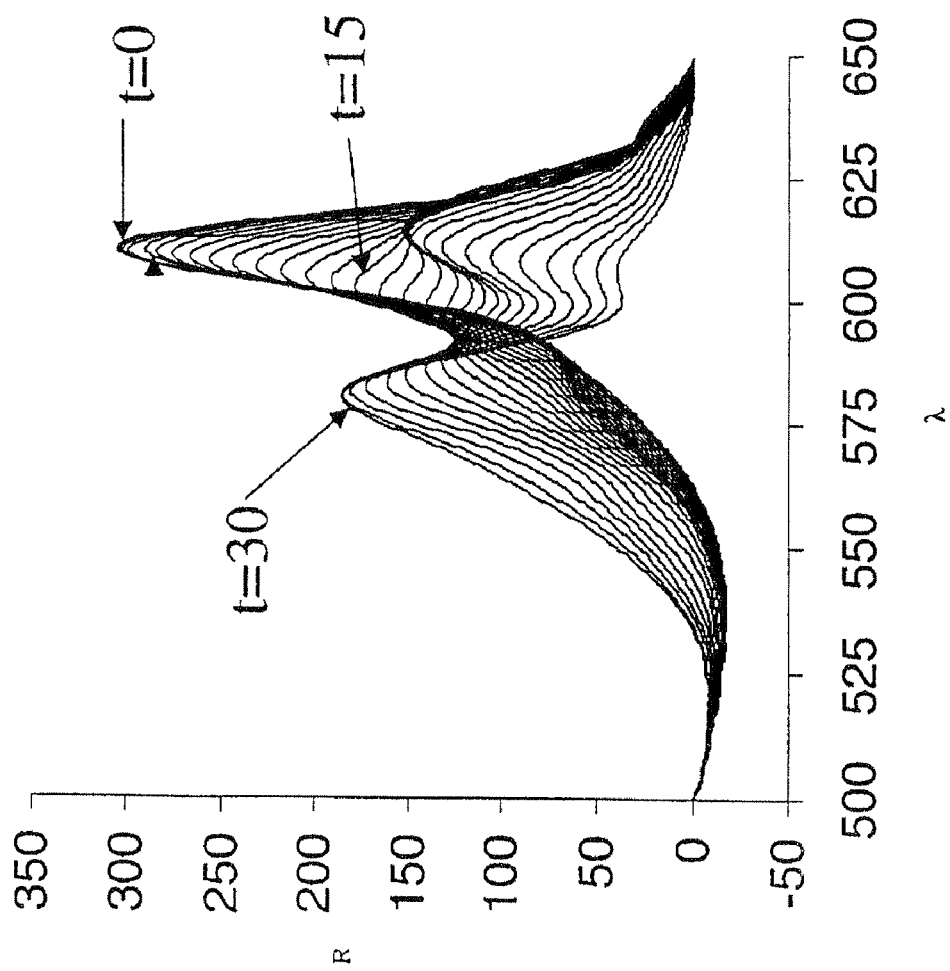
FIG. 38 shows the effect of α-amylase on a hologram.

FIG. 38 shows the effect of α-amylase on the hologram. More specifically, the graph of reflectance (R) against wavelength ($\lambda$; nm) shows degradation of the hologram. The traces are at 1 minute intervals, after the addition of 500 units amylase.

This approach may be extended to a wide range of other hydrolytic enzymes if the starch hologram is replaced by one made in a different polymer material which is cleavable by the enzyme of interest.

Example 2

An Ethanol Sensor

A microscope slide is presubbed as follows: a 1% solution of 3-(trimethoxysilyl)propyl methacrylate in dry acetone is poured over it and left overnight to evaporate and hydrolyse on the glass surface. Excess silane is removed by washing with acetone before drying.

A solution of polymerizable monomers is prepared as follows:

475 µl 2-Hydroxyethyl methacrylate (HEMA)
25 µl Ethylene dimethacrylate (EDMA)
500 µl Propan-1-ol
5 mg 2,2'-dimethoxyphenyl acetophenone (DMPAP)

100 µl of this solution is poured onto a subbed slide (laid horizontally) and covered with an inert sheet of non-stick as high density polythene of the type used for transfer lettering (Letraset). The sandwich is then exposed to UV light through the glass side until fully polymerised. After removing the polythene cover sheet, the sample is rinsed in methanol and dried in a warm air flow.

The sample is treated with silver nitrate as for Example 1, but this time it is necessary for the 0.25 M silver nitrate to be in 50% water/50% 2-propanol to enable it to readily penetrate the polymer. The slide is left in contact with the solution for an hour (even several hours was not found to be detrimental or to make any difference).

After blotting the surface and drying as before, the slide is clamped and held in a rapidly rotating solution of bromide ions made up as follows:

850 ml Methanol
0.03 g Sensitizing dye [see Example 1]
stirred until dissolved, then are added:
150 ml Water
27 g Lithium bromide In this case immersion time t(Br) is 10 minutes. The slide is then rinsed in running water.

After exposure, a developer formulation containing a large percentage of alcohol is used:

25 g Sodium hydroxide
150 ml Water
10 g Hydroquinone
850 ml Methanol

The development is stopped in a bath of:

50 ml Acetic acid
150 ml Water
800 ml Methanol

The grating consists at this stage of developed silver fringes and it can be advantageous to remove undeveloped silver bromide in a "fix". A fix solution is 10% "hypo" (sodium thiosulphate) in a 50/50 solution of methanol/water. After agitating in hypo solution for 10 minutes, residual dye in the emulsion is also removed.

Figure 39:
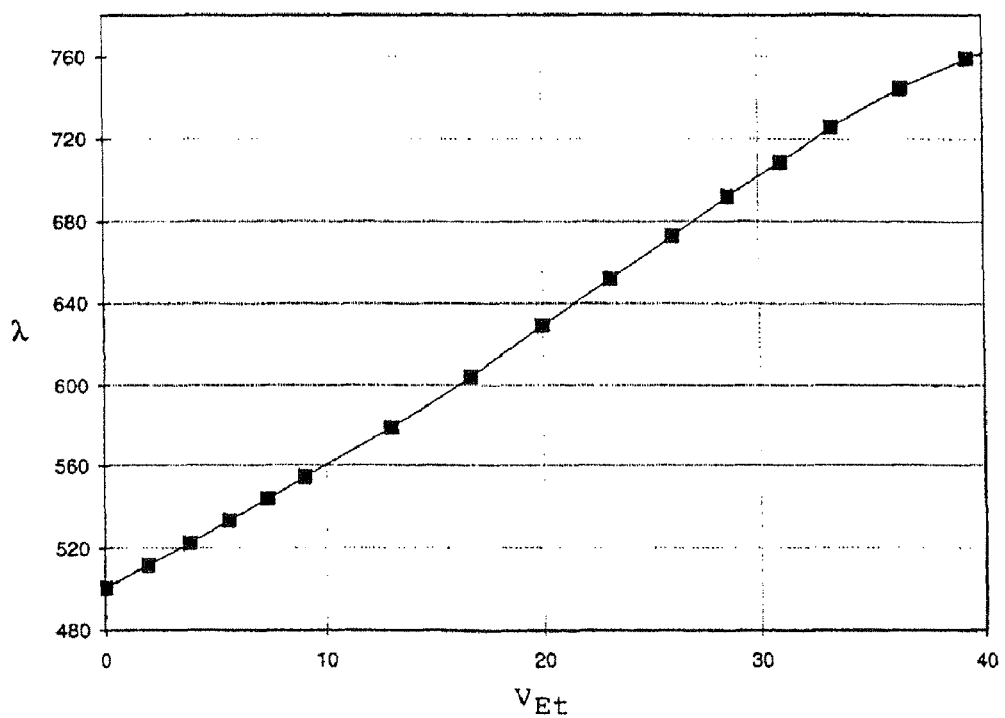
FIG. 39 is a graph of wavelength ($\lambda$; nm) against ethanol (V E1; vol %) showing a change in volume of a hologram as it is immersed in mixtures of ethanol and water.

FIG. 39 is a graph of wavelength ($\lambda$; nm) against ethanol (V E1; vol %). It shows the change in volume of this hologram as it is immersed in mixtures of ethanol and water. It can therefore he used as a sensor to monitor concentrations of ethanol.

Example 3

Na/K Sensors

Sensors capable of measuring the concentration of sodium ions in the presence of potassium ions and vice versa are made.

3 mg DMPAP dissolved in 70 µl methanol [UV initiator]
50 µl HEMA
75 µl methacryloyl ester of hydroxymethyl 12 crown 4

The liquid solution is poured over a presubbed microscope slide and the same treatment is carried out as in Example 2, to produce a grating which can be cut to suit a spectrometer cuvette or mounted at the end of a fibre optic cable. Thus the silver grating is embedded in a copolymer of methacryloyl 12 crown 4 and HEMA in the approximate mole ratio of 60:40. Since the grating is subjected to high concentrations of salt solutions during preparation, it first requires extensive rinsing in several changes of de-ionized water for at least an hour before it can be used as a sensor.

Figure 40B:
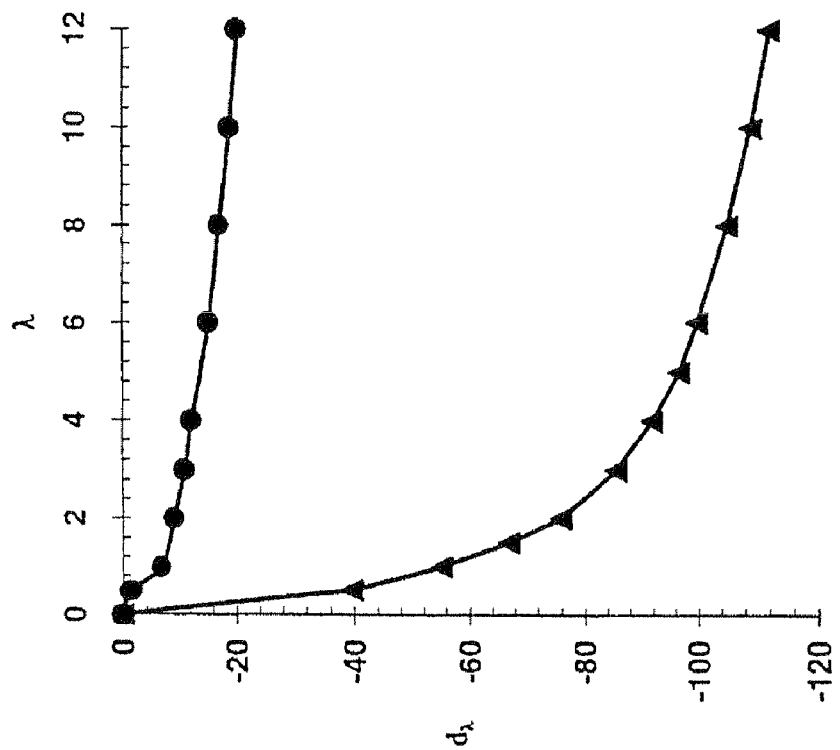
FIGS. 40a and 40b are graphs of cation concentration ([+]; mM) against wavelength shift (d$\lambda$; nm) contrasting the effects of sodium ions (●) and potassium ions (▲) on the response of a hologram.
Figure 40A:
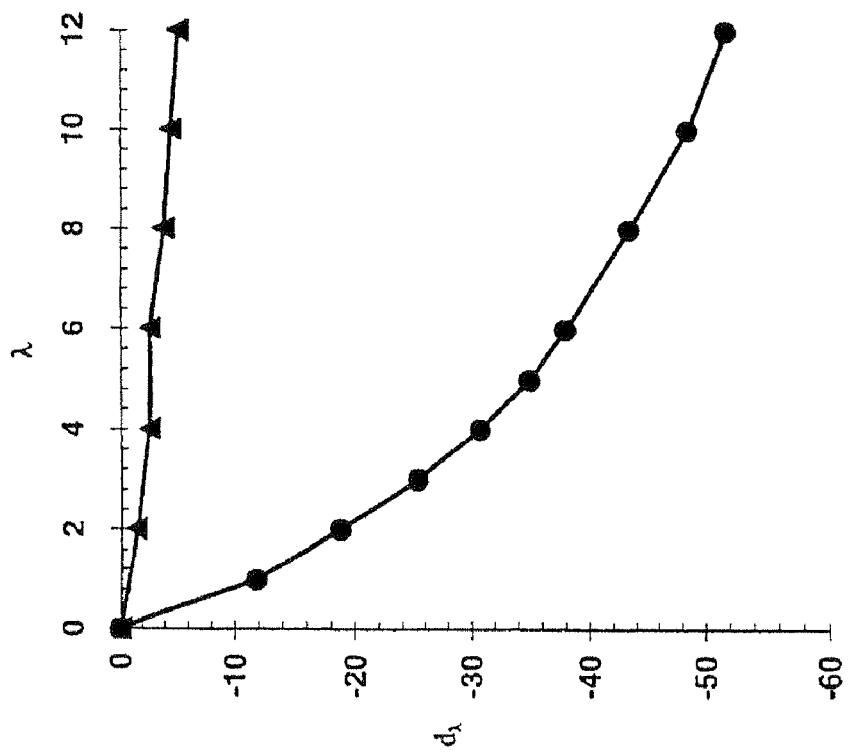

FIG. 40a is a graph of cation concentration ([+]; mM) against wavelength shift (d$\lambda$; nm). It contrasts the effects of sodium ions (●) and potassium ions (▲) on the response of the hologram.

By the same general procedure, but using the converse effect, a sensor capable of measuring potassium ions in the presence of sodium ions can be made by using a larger crown ether ring. Thus, if the 12 crown 4 compound is substituted by an equivalent quantity of the equivalent 15 crown 5 compound, the resulting grating can act as a potassium ion sensor. This is shown in FIG. 40b.

Example 4

A pH Sensor

Sensors capable of measuring the pH of a liquid over a particular range are prepared in a similar manner to Example 2, but incorporating functional monomers, which ionise over a particular pH interval. In this case, methacrylic acid (MAA) and vinyl pyridine (VP) are used. MAA is an acid and is uncharged at low pH. It ionises and becomes charged as the pH is raised. VP is charged at low pH and loses its charge as the pH is raised.

The monomer compositions used to make the films are shown in the following table:

| Identifier | HEMA (µl) | EDMA (µl) | MAA (µl) | VP (µl) | propan-1-01 (µl) | DMPAP (mg) |
|---|---|---|---|---|---|---|
| — | 475 | 25 | 0 | 0 | 500 | 5 |
| 2% MAA | 465 | 25 | 10 | 0 | 500 | 5 |
| 4% MAA | 455 | 25 | 20 | 0 | 500 | 5 |
| 6% MAA | 445 | 25 | 30 | 0 | 500 | 5 |
| 8% MAA | 435 | 25 | 40 | 0 | 500 | 5 |

-continued

| Identifier | HEMA (μl) | EDMA (μl) | MAA (μl) | VP (μl) | propan-1-ol (μl) | DMPAP (mg) |
|---|---|---|---|---|---|---|
| 10% MAA | 425 | 25 | 50 | 0 | 500 | 5 |
| 2% VP | 465 | 25 | 0 | 10 | 500 | 5 |
| 4% VP | 455 | 25 | 0 | 20 | 500 | 5 |
| 6% VP | 445 | 25 | 0 | 30 | 500 | 5 |
| 8% VP | 435 | 25 | 0 | 40 | 500 | 5 |
| 10% VP | 425 | 25 | 0 | 50 | 500 | 5 |

100 μl of each formulation is placed on a pre-subbed slide, covered with a polymer overlay and polymerised with U.V. light. The overlay is removed, and each slide is washed with methanol. 100 μl 0.3M silver perchlorate in propan-1-ol:water (1:1) is placed on each slide, which is covered with a polyester overlay to spread the liquid over the whole slide area. This is left for 5 minutes, then the overlay is removed, the surface blotted and the slide dried in warn air. Each slide is dipped in a bromide bath as described in Example 2. t(Br) was 2 minutes. After dipping, the slide is washed in running water.

During holographic exposure, it is important that the functional groups are in their non-ionised form so that the subsequent replay wavelength remains visible at all pH values. Hence MAA-containing films are exposed immersed in 1% ascorbic acid, pH3, and VP-containing films in 0.1M phosphate buffer, pH7.2. Development is with the methanolic hydroquinone developer described in Example 2.

Figure 41A:
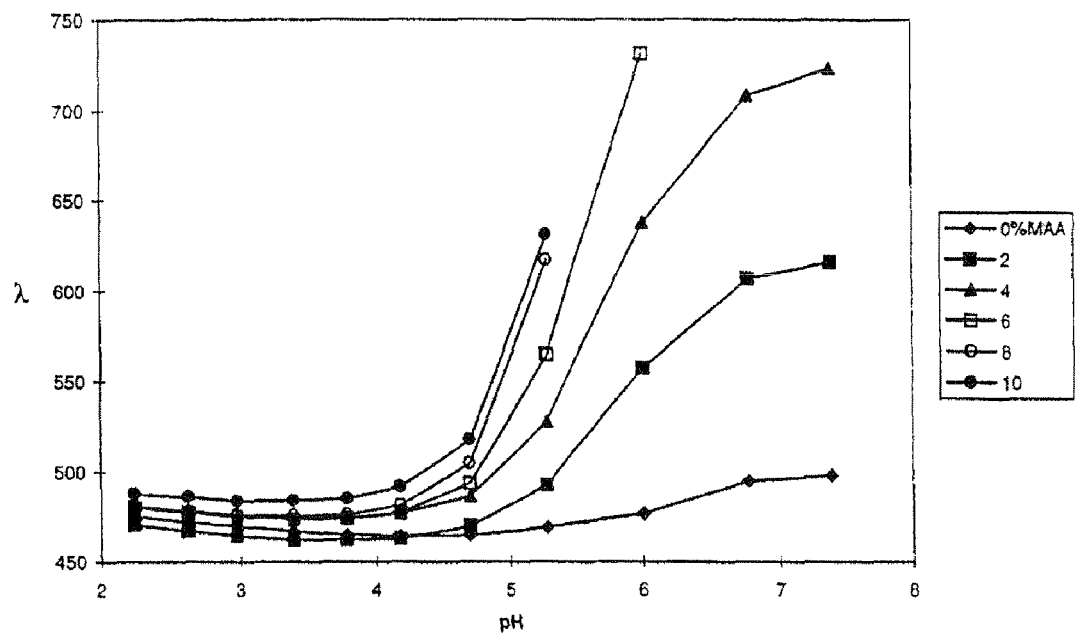
FIG. 41a is a graph of wavelength ($\lambda$; nm) against pH showing the responses of MAA-containing holograms.
Figure 41B:
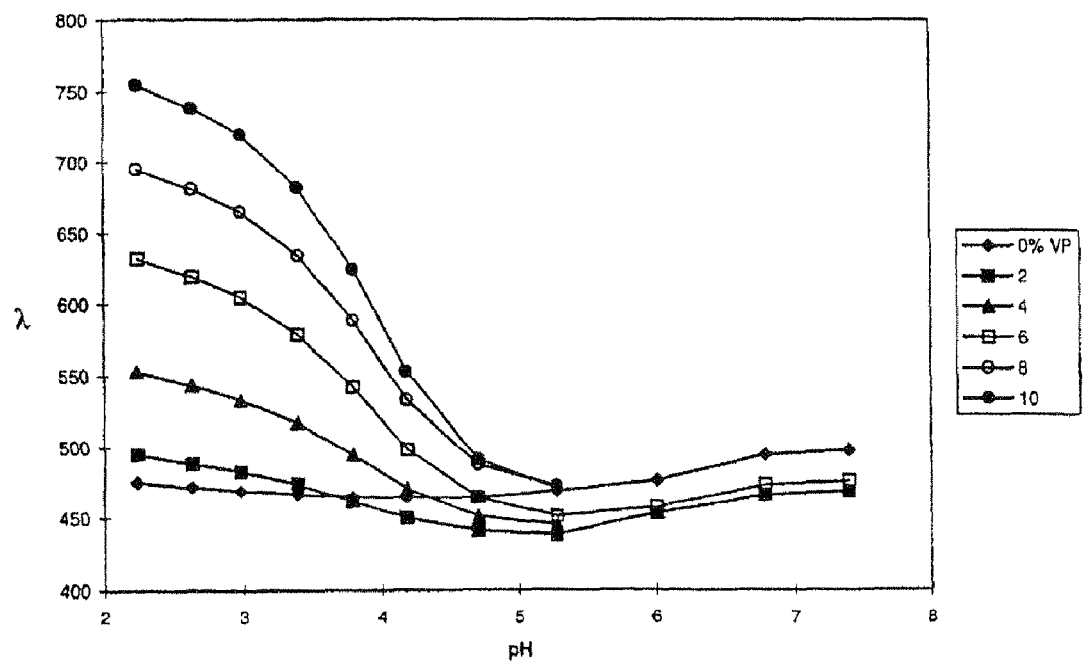
FIG. 41b is a graph of wavelength ($\lambda$; nm) against pH showing the responses of VP-containing holograms.

The holograms produced are tested in a series of citrate/phosphate buffers with conductivity normalised to 20 mS/cm using KCl. The responses of the MAA-containing holograms are shown in FIG. 41a and those for VP-containing holograms in FIG. 41b. These graphs are each of wavelength (λ; nm) against pH. It is clear that the pH interval over which the hologram responds can be changed by altering the nature of the ionising functional group in the hologram. The size of the response, for a given change in pH, can be controlled by altering the amount of ionising monomer in the hologram.

Example 5

A Periodate Sensor

170 μl of 25% w/w methacrylamide in water and 284 μl of 50% w/w acrylamide in water are mixed. 11.56 mg methylene bisacrylamide was added and dissolved, followed by 50 μl of a 4% w/w solution in water of a thioindigo vat dye in its leuco form. 100 μl of this mixture is placed on a pre-subbed slide and polymerised as for Example 2.

This is repeated twice, substituting for the methylene bisacrylamide for 14.55 mg N,N'-bisacryloylpiperazine and 15 mg 1,2-dihydroxyethylenebisacrylamide respectively.

The films are treated to introduce silver nitrate as for Example 1 and then dipped in a bromide bath as for Example 2. t(Br) is 1 minute. The films are exposed, immersed in water and developed and fixed as for Example 1.

Figure 42:
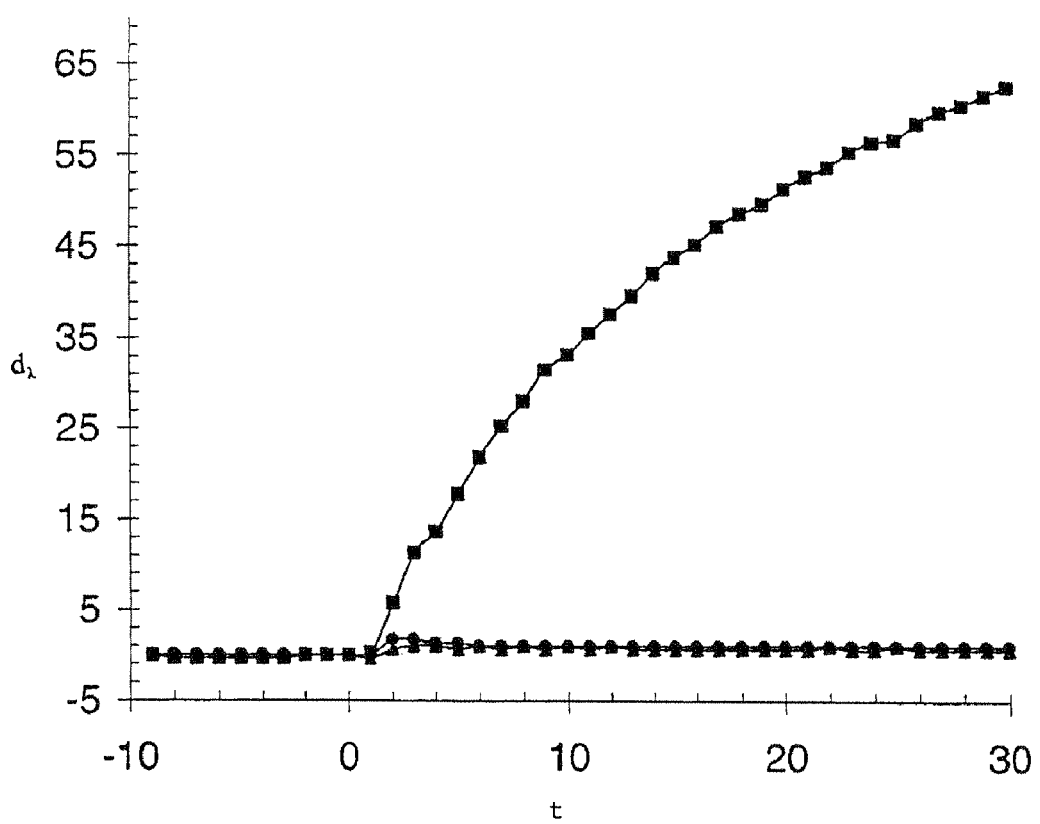
FIG. 42 is a graph of wavelength shift (d $\lambda$; nm) against time (t; min).

The resulting holograms are cut and placed in 1 ml water in cuvettes. The wavelength is monitored at 1 minute intervals for 10 minutes. Then 10 μl 0.1M NaIO 4 is added and the response monitored for 30 minutes. The results are presented in FIG. 42, a graph of wavelength shift (dλ; nm) against time (t; min). It is clear that the methylenebisacrylamide (●) and N,N'-diacryloylpiperazine (▲) cross-linked holograms are unaffected by this treatment, but that the 1,2-dihydroxyethylenebisacrylamide-containing hologram (■) is caused to swell by the cleavage of the vicinal diol functionality in the cross-linker by the periodate anion. Hence the presence of periodate can be measured by the hologram.

This Example can be extended by implication to any other chemically or biochemically cleavable cross-linker built into an otherwise more or less inert polymer film.

What is claimed is:

1. A holographic sensor, comprising: a thin film polymer matrix that undergoes a change in response to a substance to be sensed, the matrix comprising within its volume a set of two or more holographic recordings, each recording providing a holographic image when the sensor is illuminated, wherein the presence or appearance of each image is visible to a viewer's eye as a function of the response of the sensor to the substance to be sensed, and the images provide a dynamic range of the sensor, and wherein the sensor provides, in the absence of the substance, a first holographic image that is visible and a second holographic image that is invisible, and wherein, as a consequence of a wavelength shift in the presence of the substance, the first holographic image is invisible and the second holographic image is visible.

2. A sensor according to claim 1, wherein each image has a unique location in the visible or invisible spectrum.

3. A sensor according to claim 1, wherein each image is pictorial, numerical and/or alphabetical.

4. A sensor according to claim 1, wherein the first visible holographic image is representative of the substance or a scenario in which the substance is found or the sensor is used.

5. A sensor according to claim 1, wherein at least one of the first and second visible holographic images is numerical.

6. A sensor according to claim 1, wherein the first visible holographic image is alphabetical and provides a message corresponding to the substance or a scenario in which substance is found or the sensor is used.

7. A sensor according to claim 1, wherein the first visible holographic image has a location, in the space of the image, corresponding to or representative of the substance or a scenario in which the substance is found or the sensor is used.

8. A sensor according to claim 1, wherein the first visible holographic image is calibrated with respect to the quantity of the substance.

9. A sensor according to claim 1, which additionally comprises a visible scale.

10. A sensor according to claim 9, wherein the scale is invariant with respect to the concentration of the substance.

11. A sensor according to claim 1, which provides multiple images within one film.

12. A sensor according to claim 1, which provides at least three images.

13. A sensor according to claim 1, which comprises a plurality of films each providing its own dynamic range within the dynamic range of the sensor.

14. A sensor according to claim 1, which comprises a plurality of films each responding to a different substance.

15. A sensor according to claim 1, which additionally comprises colour transmission filter.

16. A sensor according to claim 1, where the first visible holographic image is formed from a set of visible pixels, the pattern of pixels being indicative or representative of the substance or a scenario in which the substance is found or the sensor is used.

17. Apparatus comprising a sensor according to claim 1 and an illumination source.

18. A sensor comprising: a matrix that undergoes changes in response to a substance to be sensed, the matrix comprising within its volume multiplexed holographic images including a first holographic image having a first peak wavelength and a second holographic image different from the first holographic image having a second peak wavelength different from the first peak wavelength, wherein, in the presence of the substance during a sensing operation, the first peak wavelength, but not the second peak wavelength, is in a visible range, whereby the first holographic image, but not the second holographic image is visible, and wherein, in the absence of the substance during the sensing operation, the second peak wavelength, but not the first peak wavelength, is in a visible range and the second holographic image, but not the first holographic image, is visible.

19. A sensor according to claim 18, wherein the multiplexed holographic images are embodied in a single polymer film.

20. A sensor according to claim 18, wherein the multiplexed holographic images are embodied in multiple polymer films.

21. A sensor according to claim 18, wherein the multiplexed holographic images comprise a third holographic image different from the first and second holographic images, the third holographic image having a peak wavelength in the visible range regardless of the presence or absence of the substance during the sensing operation.

22. A sensor according to claim 21, wherein the third holographic image comprises a scale.

23. A sensor according to claim 18, wherein the first image and the second image differ in one or more of pictorial, numerical and alphabetical features.

24. A method for making a holographic sensor containing a first recorded holographic image and a second recorded holographic image that are multiplexed in a matrix, the method comprising:

providing a matrix that has a plurality of states that are affected by a substance to be sensed;

recording within the volume of the matrix a first holographic image when the matrix is in a first state, the first holographic image having a first peak wavelength;

recording within the volume of the matrix a second holographic image when the matrix is in a second state that is different from the first state, the second holographic image having a second peak wavelength different from the first peak wavelength;

wherein when the matrix is in the first state, the first peak wavelength, but not the second peak wavelength, is in the visible range, whereby the first recorded holographic image, but not the second recorded holographic image is visible; and when the matrix is in the second state, the second peak wavelength, but not the first peak wavelength, is in the visible range and the second recorded holographic image recorded, but not the first recorded holographic image is visible.

25. The method of claim 24, wherein the first state and the second state are different states of swelling.

26. The method of claim 25, wherein the state of swelling is controlled by pH, ion concentration, humidity or water activity.

27. The method of claim 24, wherein the first state and the second state are different states of thickness of the matrix.

28. The method of claim 24, further comprising recording within the volume of the matrix a third holographic image when the matrix is in a third state.

29. A method for detecting a substance in a sample comprising:

sensing a sample, the sensing being done by a sensor exposed to the sample, the sensor comprising a matrix that undergoes changes in response to a substance to be sensed, the matrix comprising within its volume multiplexed holographic images including a first holographic image having a first peak wavelength and a second holographic image different from the first holographic image having a second peak wavelength different from the first peak wavelength, wherein, in the presence of the substance during a sensing operation, the first peak wavelength, but not the second peak wavelength, is in a visible range, whereby the first holographic image, but not the second holographic image is visible, and wherein, in the absence of the substance during the sensing operation, the second peak wavelength, but not the first peak wavelength, is in a visible range and the second holographic image, but not the first holographic image, is visible; and replaying the holographic image by the sensor, wherein replay of the first holographic image, but not the second holographic image, is indicative of the presence of the substance in the sample.

30. A method for detecting a substance in a sample comprising:

sensing a sample, the sensing being done by a sensor exposed to the sample, the sensor comprises a thin film polymer matrix that undergoes a change in response to a substance to be sensed, the matrix comprising within its volume a set of two or more holographic recordings, each recording providing a holographic image when the sensor is illuminated, wherein the presence or appearance of each image is visible to a viewer's eye as a function of the response of the sensor to the substance to be sensed, and the images provide a dynamic range of the sensor, and wherein the sensor provides, in the absence of the substance, a first holographic image that is visible and a second holographic image that is invisible, and wherein, as a consequence of a wavelength shift in the presence of the substance, the first holographic image is invisible and the second holographic image is visible; and replaying the holographic image by the sensor when the sensor is illuminated, wherein replay of the second holographic image, but not the first holographic image, is indicative of the presence of the substance in the sample.

* * * * *